United States Patent
Luo et al.

(10) Patent No.: US 9,617,269 B2
(45) Date of Patent: Apr. 11, 2017

(54) N-SUBSTITUTED PYRAZOLO [3,4-D] PYRIMIDINE KETONE COMPOUND, AND PREPARATION PROCESS AND USE THEREOF

(71) Applicants: SUN YAT-SEN UNIVERSITY, Guangdong (CN); UNIVERSITY OF NORTH CAROLINA AT CHAPEL HILL, Chapel Hill, NC (US)

(72) Inventors: Haibin Luo, Guangdong (CN); Yiqian Wan, Guangdong (CN); Hengming Ke, Chapel Hill, NC (US); Peiqing Liu, Guangdong (CN); Manna Huang, Guangdong (CN); Yongxian Shao, Guangdong (CN); Xinhai Zhu, Guangdong (CN); Yinghong Cai, Guangdong (CN); Yuguo Liu, Guangdong (CN)

(73) Assignees: Sun Yat-Sen University, Guangzhou, Guangdong (CN); University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/420,530

(22) PCT Filed: Aug. 2, 2013

(86) PCT No.: PCT/CN2013/080725
§ 371 (c)(1),
(2) Date: Feb. 9, 2015

(87) PCT Pub. No.: WO2014/023191
PCT Pub. Date: Feb. 13, 2014

(65) Prior Publication Data
US 2015/0218168 A1    Aug. 6, 2015

(30) Foreign Application Priority Data
Aug. 8, 2012    (CN) .......................... 2012 1 0280123

(51) Int. Cl.
C07D 487/00    (2006.01)
C07D 487/04    (2006.01)
A61K 31/519    (2006.01)

(52) U.S. Cl.
CPC .......... *C07D 487/04* (2013.01); *A61K 31/519* (2013.01)

(58) Field of Classification Search
None
See application file for complete search history.

(56) References Cited

U.S. PATENT DOCUMENTS

2006/0111372 A1    5/2006    Hendrix et al.

FOREIGN PATENT DOCUMENTS

| CN | 1177960 A | 4/1998 | |
| CN | 102260266 A | 11/2011 | |
| CN | 102786525 A | 11/2012 | |
| CN | 102260266 | * 8/2013 | ............. A61P 31/00 |
| WO | 9628429 A1 | 9/1996 | |
| WO | 0129045 A1 | 4/2001 | |

(Continued)

OTHER PUBLICATIONS

Meng, et. al., Journal of Medicinal Chemistry (2012), 55(19), 8549-8558.*

(Continued)

*Primary Examiner* — Jeffrey H Murray
(74) *Attorney, Agent, or Firm* — Hamre, Schumann, Mueller & Larson, P.C.

(57) ABSTRACT

Disclosed are an N-substituted pyrazolo [3,4-d] pyrimidine ketone compound of formula (I), and a preparation process and use thereof as a phosphodiesterase IX (PDEIX) inhibitor:

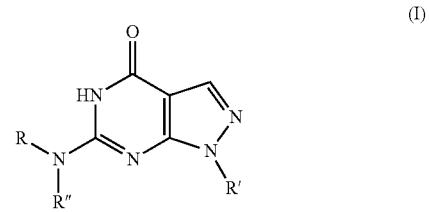

wherein

R' is selected from isopropyl, cyclopentyl, cyclohexyl, isobutyl, and o-chlorophenyl;

when R"=CH$_3$, R represents benzyl; and when R"=H, R is selected from 3-methylpyridine, 1-phenylethyl, 1-(4-chlorophenyl)ethyl,

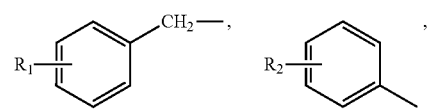

D- or L-configured CHCH$_3$CONHR''', D- or L-configured CH$_2$CONHR''', D- or L-configured CH$_2$CH$_2$CONHR'''; wherein R$_1$ is selected from hydrogen, chlorine, methoxy, methyl, trifluoromethyl, dimethoxy, methylenedioxy, and dichlorine, and R$_2$ is selected from hydrogen, methoxy, ethoxy, isopropoxy, methyl, dimethoxy, and 2-methyl-4-methoxy, and wherein R''' is p-methoxyphenyl.

5 Claims, No Drawings

(56) References Cited

FOREIGN PATENT DOCUMENTS

| WO | 03037432 A1 | 5/2003 |
|----|----|----|
| WO | 03037899 A1 | 5/2003 |
| WO | 2004096811 A1 | 11/2004 |
| WO | 2004113306 A1 | 12/2004 |
| WO | 2008055959 A1 | 5/2008 |
| WO | 2008071650 A2 | 6/2008 |
| WO | 2009071707 A1 | 6/2009 |
| WO | 2012004900 A1 | 1/2012 |
| WO | 2012020022 A1 | 2/2012 |
| WO | 2012033101 A1 | 3/2012 |
| WO | 2012033144 A1 | 3/2012 |
| WO | 2012040230 A1 | 3/2012 |

OTHER PUBLICATIONS

Fisher et al.: "Isolation and Characterization of PDE9A, a Novel Human cGMP-specific Phosphodiesterase"; The Journal of Biological Chemistry, 1998, vol. 273, pp. 15559-15564.

Wunder et al.: "Charcaterization of the First Potent and Selective PDE9 Inhibitor Using a cGMP reporter Cell Line"; Molecular Pharmacology, 2005, vol. 68, pp. 1775-1781.

International search report for International application No. PCT/CN2013/080725, dated Nov. 7, 2013 (12 pages).

\* cited by examiner

N-SUBSTITUTED PYRAZOLO [3,4-D] PYRIMIDINE KETONE COMPOUND, AND PREPARATION PROCESS AND USE THEREOF

TECHNICAL FIELD

The present invention relates to a phosphodiesterase IX (PDEIX) inhibitor, and in particular, relates to a novel N-substituted pyrazolo [3,4-d] pyrimidine ketone compound, and a preparation process and use thereof.

BACKGROUND

Phosphodiesterase (PDE) denotes a species of proteases, and is capable of selectively degrading the second massagers, cyclic adenosine monophosphate (cAMP) and cyclic guanosine monophosphate (cGMP) in human bodies to the corresponding adenosine monophosphates to exert important physiological functions. Till now, 11 families of phosphodiesterases have been reported, wherein the phosphodiesterase IX (PDEIX) is capable of hydrolyzing the cGMP with a high specificity, and is widely distributed in human bodies (*J Bio Chem*, 1998, 273(25) 15559-15564). A PDEIX inhibitor is capable of inhibiting the enzymolysis effect on the cGMP by the PDEIX, and thus improving the cGMP level. In this way, the effects of NO and insulin are magnified, and the effects of dilating arteries are exerted, metabolization is speeded up, and atherosclerosis is resisted (WO03037432). Researches show that the cGMP plays an important role on the improvement of the cognitive ability of the human being. These characteristics render the phosphodiesterase IX to be a new target spot for the treatment of diabetes, obesity and cardiovascular diseases, and for the improvement of attention, cognitive abilities, learning and memory.

In 2005, Frank Wunder (*Mol Pharmacol*, 2005, 68: 1775-1781) reported the first PDEIX selective inhibitor BAY 73-6691. This discovery promotes people's commitments on research into the PDEIX selective inhibitor. The phosphodiesterase IX inhibitors discovered in recent years have better phosphodiesterase IX and achieve better pharmacological activity. International Patents WO2003037899, WO2004096811, and WO2012020022 have disclosed a pyrazole pyrimidine ketone-parented PDEIX inhibitor and a process for preparing the same; WO2004113306 has disclosed a cyano pyrimidine ketone-parented PDEIX inhibitor and a process for preparing the same; WO2004096811 and WO2012040230 have disclosed an imidazole trinitrogen heterocyclic ketone-parented PDEIX inhibitor and a process for preparing the same; WO2012004900 has disclosed a thienopyrimidine-parented PDEIX inhibitor and a process for preparing the same; WO2012033101 and WO201203314 have disclosed an imidazo quinoline ketone-parented PDEIX inhibitor and a process for preparing the same; and WO2004096811 has disclosed a PDEIX inhibitor using other ketone compounds as a matrix and a process for preparing the same, wherein the ketone compounds comprise imidazolyl pyrimidine ketone, oxazole pyrimidine ketone, and thiazole pyrimidine ketone. In 2011, our research group disclosed a 6-position-N-substituted pyrazolo pyrimidine ketone-parented PDEIX inhibitor having better inhibition activity and a preparation process thereof (CN102260266A).

SUMMARY

The present invention is directed to providing a high activity and high selectivity novel phosphodiesterase IX inhibitor, and providing an N-substituted pyrazolo [3,4-d] pyrimidine ketone compound, and a preparation method and use thereof.

The present invention is implemented by the following technical solutions:

The present invention provides an N-substituted pyrazolo [3,4-d] pyrimidine ketone compound of formula (I):

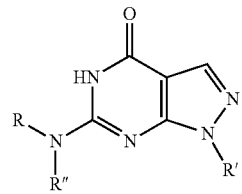

(I)

wherein

R' is selected from isopropyl, cyclopentyl, cyclohexyl, and isobutyl;

when R''=CH$_3$, R represents benzyl; and when R''=H, R is selected from 3-methylpyridine, 1-phenylethyl, 1-(4-chlorophenyl)ethyl,

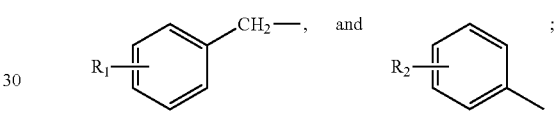

wherein R$_1$ is selected from hydrogen, chlorine, methoxy, methyl, trifluoromethyl, dimethoxy, methylenedioxy, and dichlorine, and R$_2$ is selected from hydrogen, methoxy, ethoxy, isopropoxy, methyl, dimethoxy, and 2-methyl-4-methoxy.

Preferably, when R''=H, the compound is selected from compounds of formulas (II), (III), (IV), and (V):

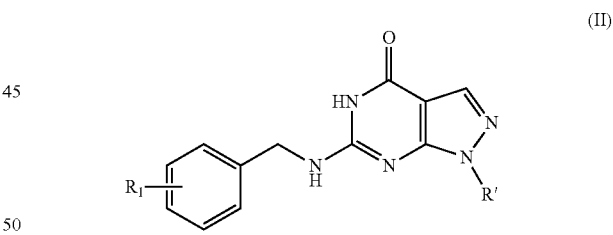

(II)

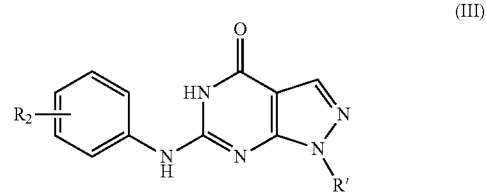

(III)

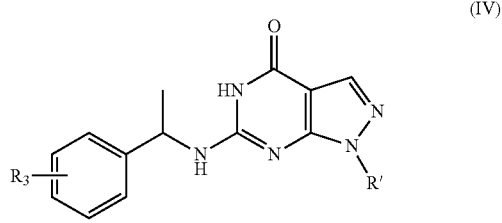

(IV)

-continued (V)

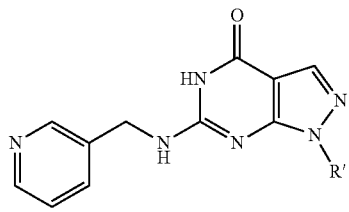

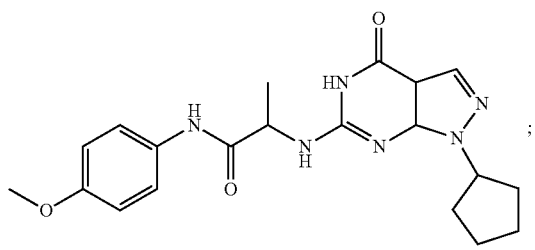
(VIII)

(IX)

wherein

R' is selected from isopropyl, cyclopentyl, cyclohexyl, and isobutyl;

R1 in formula (II) is selected from hydrogen, methyl, methoxy, 2,4-dimethoxy, 3,4-methylenedioxy, chlorine, 2,4-dichlorine, and trifluoromethyl;

$R_2$ in formula (III) is selected from hydrogen, methyl, methoxy, ethoxy, isopropoxy, 2-methyl-4-methoxy, and 2,5-dimethoxy; and $R_3$ in formula (IV) is selected from hydrogen and chlorine.

The present invention provides an N-substituted pyrazolo [3,4-d] pyrimidine ketone compound of formula (VI):

(VI)

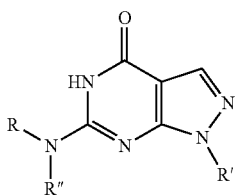

wherein

R' is selected from isopropyl or cyclopentyl, cyclohexyl, isobutyl, and o-chlorophenyl;

when R''=CH$_3$, R represents benzyl; and when R''=H, R is selected from D- or L-configured CHCH$_3$CONHR''', D- or L-configured CH$_2$CONHR''', D- or L-configured CH$_2$CH$_2$CONHR''', wherein R''' is p-methoxyphenyl.

Preferably, the N-substituted pyrazolo [3,4-d] pyrimidine ketone compound according to the present invention is selected from compounds of formulas (VII), (VIII), (IX), (X), and (XI):

(VII)

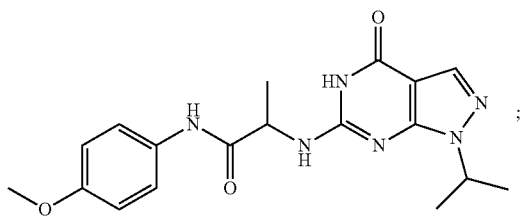

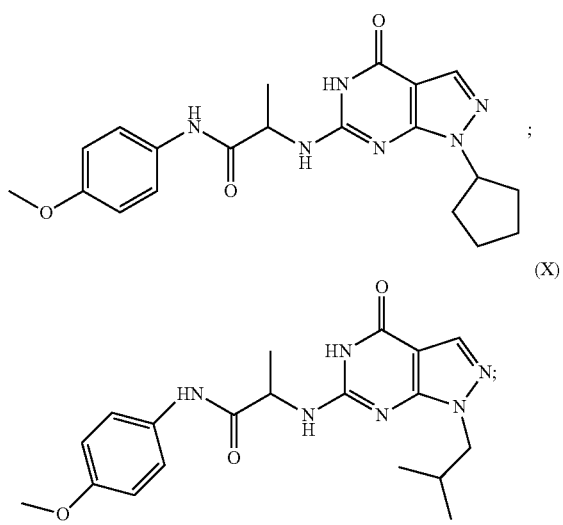

(X)

(XI)

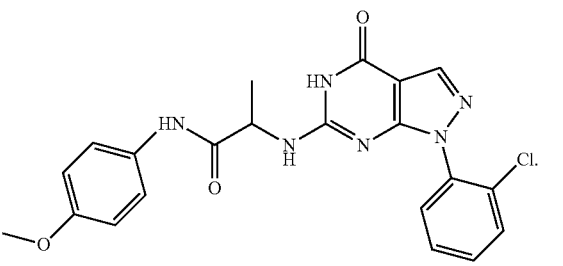

The present invention provides a process for the preparation of an N-substituted pyrazolo [3,4-d] pyrimidine ketone compound, comprising the following steps:

(1) reacting using 2,4,6-trichloro-5-pyrimidinecarbaldehyde and hydrazine having a substituent group as starting materials, triethylamine as a base, and ethanol as a solvent at temperature −78° C. to obtain a compound A, wherein a molar ratio of 2,4,6-trichloro-5-pyrimidinecarbaldehyde to hydrazine to triethylamine is 1:1-1.1:2-3, and 2,4,6-trichloro-5-pyrimidinecarbaldehyde has a concentration of 0.05 to 1.0 mol/L;

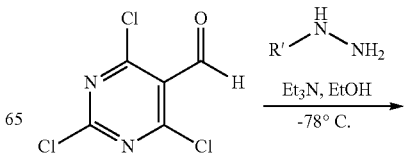

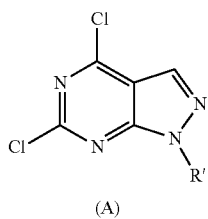

(2) hydrolyzing the compound A under a basic condition to obtain a compound B, wherein the basic condition comprises sodium hydroxide and potassium hydroxide, a molar ration of A to a base is 1:10-40, and A has a concentration of 0.05 to 0.5 mol/L; and

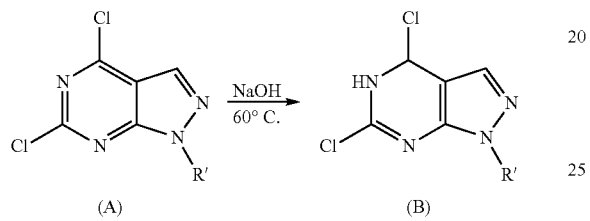

(3) reacting the compound B with an amine compound in the presence of triethylamine as a base to obtain a target compound I, wherein a molar ratio of B to triethylamine to the amino compound is 1:1.3:1.2-3, and B has a concentration of 0.05 to 0.5 mol/L.

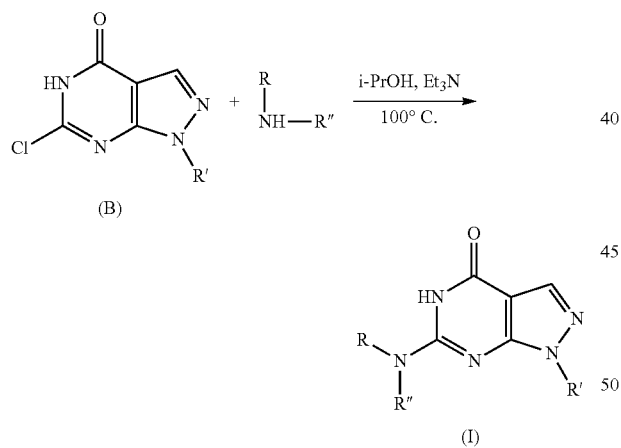

The N-substituted pyrazolo [3,4-d] pyrimidine ketone compound according to the present invention has a better inhibition effect on a phosphodiesterase IX, and may be used as a selective inhibitor of the phosphodiesterase.

The N-substituted pyrazolo [3,4-d] pyrimidine ketone compound according to the present invention may be used for the treatment of diabetes, obesity and cardiovascular diseases, and for the improvement of attention, cognitive abilities, learning and memory.

The preparation method according to the present invention has the advantages of quickness, convenience, low cost, and the like.

DETAILED DESCRIPTION

The present invention is hereinafter described in detail, but is not limited to the following description.

I. Instruments and Medicaments

The nuclear magnetic resonance spectrum (NMR) in the present invention is tested by the instrument AVANCE 400 manufactured by Bruker in Germany, and a solvent residual peak is used as an internal standard; the mass spectrum is tested by the instrument LCMS-2010A (ESI source) manufactured by Shimadzu Corporation in Japan; the chemical reagents are purchased from Guangzhou Ai Er Lu Chemicals Company, J&K Corporation, Alfar-Aser Corporation, Aladdin Chemical Regents Corporation, and so on; and the silica gel for column chromatography is purchased from Qingdao Haiyang Chemical Co., Ltd.

Example 1

Synthesis of Compound M-1 of Formula (M-1)

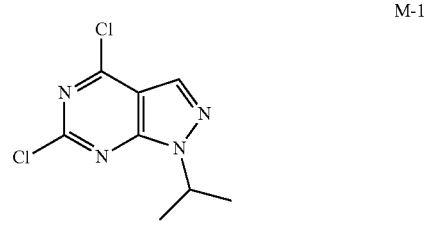

2,4,6-trichloro-5-pyrimidinecarbaldehyde (424 mg, 2 mmol), isopropylhydrazine hydrochloride (221 mg, 2 mmol), triethylamine (505 mg, 5 mmol) were reacted in ethanol (40 ml) at temperature −78° C. for 2 hours; the temperature was raised to room temperature, and the mixture was further reacted for 8 hours; the solvent was removed by rotatary evaporation, and the reaction product was extracted using ethyl acetate and dried by anhydrous sodium sulfate; the solvent was evaporated by reducing the pressure and the reaction product was separated and purified through rapid column chromatography; finally 323 mg white solids were obtained, and the yield was 70%.

MS (ESI$^+$): m/z: 231 ([M+H]$^+$); $^1$H NMR (400 MHz, CDCl$_3$) δ 8.13 (s, 1H), 5.16 (hept, J=6.8 Hz, 1H), 1.57 (d, J=6.7 Hz, 6H).

Example 2

Synthesis of Compound M-2 of Formula (M-2)

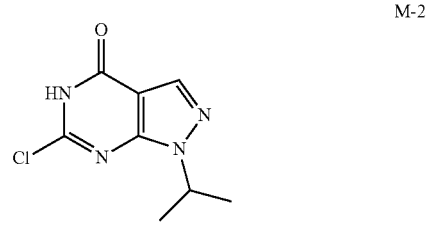

At 60° C., compound M-1 (231 mg, 1 mmol) obtained in Example 1 was added into 20 ml 1 mol/L NaOH aqueous solution, and stirred for 1 hour for reaction. After the reaction, the pH was adjusted to 5 to 6 using glacial acetic acid, and white solids then precipitated; the reaction product was subjected to sucking filtration, washing, and drying; finally, 162 mg white solids were obtained, and the yield was 76%.

MS (ESI⁻): m/z: 211 ([M−H]⁻); ¹H NMR (400 MHz, CDCl₃) δ 8.12 (s, 1H), 5.01 (hept, J=6.7 Hz, 1H), 1.54 (d, J=6.7 Hz, 6H).

Example 3

Synthesis of Compound M-3 of Formula (M-3)

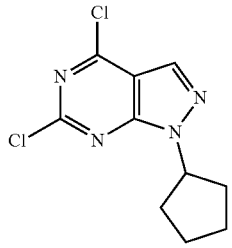

M-3

The synthesis method was the same as that for the method for the synthesis of compound M-1 in Example 1. 2,4,6-trichloro-5-pyrimidinecarbaldehyde (424 mg, 2 mmol), cyclopentylhydrazine hydrochloride (300 mg, 2.2 mmol), triethylamine (404 mg, 4 mmol) were reacted in ethanol (2 ml); the reaction product was separated and purified; finally, 374 mg white solids were obtained, and the yield was 73%.

MS (ESI⁺): m/z: 231 ([M+H]⁺); ¹H NMR (400 MHz, CDCl₃) δ 8.14 (s, 1H), 5.36-5.26 (m, 1H), 2.25-2.07 (m, 4H), 2.05-1.94 (m, 2H), 1.82-1.71 (m, 2H).

Example 4

Synthesis of Compound M-4 of Formula (M-4)

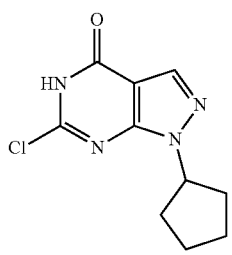

M-4

The synthesis method was the same as that for the method for the synthesis of compound M-2 in Example 2. Compound M-3 (257 mg, 1 mmol) and 2 ml 5 mol/L NaOH aqueous solution were reacted; finally, 410 mg white solids were obtained, and the yield was 86%.

MS (ESI⁻): m/z: 237 ([M−H]⁻); ¹H NMR (400 MHz, CDCl₃) δ 8.10 (s, 1H), 5.15 (p, J=7.5 Hz, 1H), 2.20-2.04 (m, 4H), 2.02-1.91 (m, 2H), 1.72 (ddd, J=11.2, 7.8, 3.2 Hz, 2H).

Example 5

Synthesis of Compound M-5 of Formula (M-5)

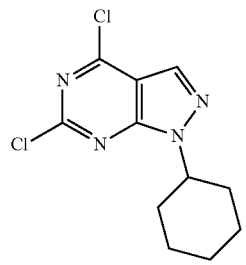

M-5

The synthesis method was the same as that for the method for the synthesis of compound M-1 in Example 1. 2,4,6-trichloro-5-pyrimidinecarbaldehyde (424 mg, 2 mmol), cyclohexylhydrazine hydrochloride (301 mg, 2 mmol), triethylamine (606 mg, 6 mmol) were reacted in ethanol (10 ml); the reaction product was separated and purified; finally, 690 mg white solids were obtained, and the yield was 64%.

MS (ESI⁺): m/z: 271 ([M+H]⁺); ¹H NMR (400 MHz, CDCl₃) δ 8.12 (s, 1H), 4.81-4.70 (m, 1H), 2.05-1.90 (m, 6H), 1.81-1.72 (m, 1H), 1.58-1.46 (m, 2H), 1.38-1.26 (m, 1H).

Example 6

Synthesis of Compound M-6 of Formula (M-6)

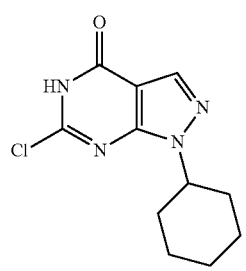

M-6

The synthesis method was the same as that for the method for the synthesis of compound M-2 in Example 2. Compound M-5 (271 mg, 1 mmol) and 5 ml 2 mol/L NaOH aqueous solution were reacted; finally, 318 mg white solids were obtained, and the yield was 63%.

MS (ESI⁻): m/z: 251 ([M−H]⁻); 1H NMR (400 MHz, DMSO) δ 13.13 (brs, 1H), 8.06 (s, 1H), 4.55-4.39 (m, 1H), 1.91-1.79 (m, 6H), 1.68 (d, J=12.6 Hz, 1H), 1.53-1.38 (m, 2H), 1.24 (ddd, J=12.8, 9.5, 3.2 Hz, 1H).

Example 7

Synthesis of Compound M-7

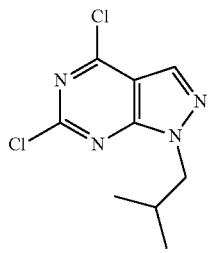

M-7

The synthesis method was the same as that for the method for the synthesis of compound M-1 in Example 1. 2,4,6-trichloro-5-pyrimidinecarbaldehyde (424 mg, 2 mmol), isobutylhydrazine hydrochloride (249 mg, 2 mmol), triethylamine (505 mg, 5 mmol) were reacted in ethanol (25 ml); the reaction product was separated and purified; finally, 378 mg white solids were obtained, and the yield was 77%.

MS (ESI+): m/z: 231 ([M+H]+); $^1$H NMR (400 MHz, CDCl$_3$) δ 8.14 (s, 1H), 4.26 (d, J=7.3 Hz, 2H), 2.38 (dp, J=13.8, 6.9 Hz, 1H), 0.93 (d, J=6.7 Hz, 6H).

Example 8

Synthesis of Compound M-8

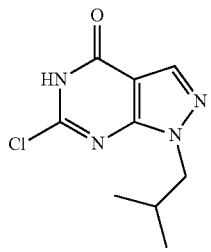

M-8

The synthesis method was the same as that for the method for the synthesis of compound M-2 in Example 2. Compound M-7 (245 mg, 1 mmol) and 10 ml 4 mol/L NaOH aqueous solution were reacted; finally, 350 mg white solids were obtained, and the yield was 77%.

MS (ESI−): m/z: 225 ([M−H]−); $^1$H NMR (400 MHz, CDCl$_3$) δ 12.45 (brs, 1H), 8.11 (s, 1H), 4.13 (d, J=7.4 Hz, 2H), 2.33 (dp, J=13.8, 6.9 Hz, 1H), 0.92 (d, J=6.7 Hz, 6H).

Example 9

Synthesis of Compound M-9

The synthesis method was the same as that for the method for the synthesis of compound M-1 in Example 1. The reaction product was separated and purified, and finally, brown solids were obtained (180 mg, 30%).

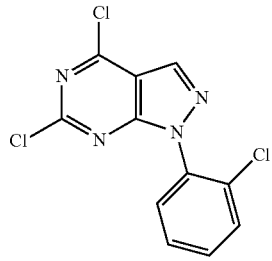

M-9

MS (ESI+): m/z: 298 ([M+H]+); $^1$H NMR (400 MHz, CDCl$_3$) δ 8.14 (s, 1H), 7.55-7.46 (m, 2H), 7.42-7.29 (m, 2H).

Example 10

Synthesis of Compound M-10

The synthesis method was the same as that for the method for the synthesis of compound M-2 in Example 2. Finally, white solids were obtained (168 mg, 60%).

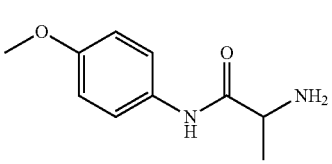

M-10

MS (ESI−): m/z: 279 ([M−H]−); $^1$H NMR (400 MHz, CDCl$_3$) δ 12.45 (brs, 1H), 8.11 (s, 1H), 7.53-7.45 (m, 2H), 7.41-7.29 (m, 2H).

Example 11

Synthesis of Compound M-11-D

M-11-D

D-alanine (890 mg, 10 mmol), di-tert-butyl dicarbonate (2616 mg, 12 mmol), and triethylamine (1515 mg, 15 mmol) were reacted in a mixed solution of water and 1,4-dioxane at room temperature for 8 hours; the solvent is removed by rotatary evaporation, and the reaction product was extracted using ethyl acetate and dried by anhydrous sodium sulfate; the solvent was evaporated by reducing the pressure; finally a light yellow thick crude product was obtained; the obtained crude product was directly put into the next reaction instead of being further purified. A DMF solution of p-methoxyaniline (1230 mg, 10 mmol) and 1-methylimidazole (820 mg, 10 mmol) were added; and at 0° C., dethyl chlorophosphate (1725 mg, 10 mmol) was dropwise added to a three-necked flask. After the dropwise adding, the reaction temperature was naturally raised to the room temperature. The reaction was stopped after the substances were sufficiently reacted. Subsequently, a saturated NaHCO$_3$ aqueous solution was added until no bubbles were generated, and then solids precipitated. The reaction product was filtered, and then watered using a small amount of water and dried. Finally, white solids were obtained. The obtained white solids were dissolved in 30 ml methanol, and under an ice bath condition, an HCL gas was given to the solution. The reaction was stopped after the substances were sufficiently reacted. The obtained crude product was separated and purified via column chromatography (DCM:MeOH=15:1), and finally a colorless oil-like substance was obtained (400 mg, 21%).

MS (ESI$^+$): m/z: 195 ([M+H]$^+$); $^1$H NMR (300 MHz, DMSO) δ 7.54 (d, J=8.9 Hz, 2H), 6.85 (d, J=8.9 Hz, 2H), 3.70 (s, 3H), 3.42 (dd, J=13.7, 6.8 Hz, 1H), 2.83 (s, 2H), 1.22 (d, J=6.9 Hz, 3H).

Example 12

Synthesis of Compound M-11-L

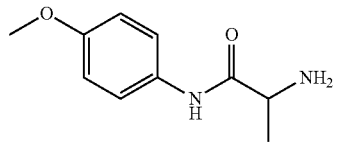

M-11-L

L-alanine was used as the starting material, and the synthesis method was the same as that for the method for the synthesis of compound M-11-D in Example 11. The reaction product was separated and purified, and finally, a colorless oil-like substance was obtained (420 mg, 22%).

MS (ESI$^+$): m/z: 195 ([M+H]$^+$); $^1$H NMR (300 MHz, CDCl$_3$) δ 9.31 (brs, 1H), 7.48-7.41 (m, 2H), 6.84-6.77 (m, 2H), 3.74 (s, 3H), 3.54 (q, J=7.0 Hz, 1H), 1.80 (s, 2H), 1.37 (d, J=7.0 Hz, 3H).

Example 13

Synthesis of Compound M-12

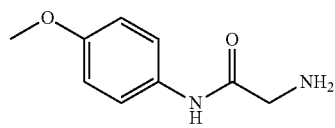

M-12

Glycine was used as the starting material, and the synthesis method was the same as that for the method for the synthesis of compound M-11-D in Example 11. The reaction product was separated and purified, and finally, a colorless oil-like substance was obtained (380 mg, 21%).

MS (ESI$^+$): m/z: 181 ([M+H]$^+$); $^1$H NMR (300 MHz, DMSO) δ 9.81 (brs, 1H), 7.52 (d, J=8.8 Hz, 2H), 6.85 (d, J=8.9 Hz, 2H), 3.70 (s, 3H), 3.24 (s, 2H), 2.67 (brs, 2H).

Example 14

Synthesis of Compound M-13

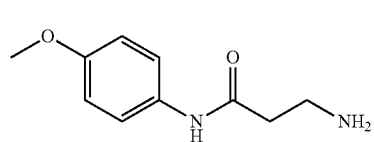

M-13

The synthesis method was the same as that for the method for the synthesis of compound M-11-D in Example 11. The reaction product was separated and purified, and finally, a colorless oil-like substance was obtained (400 mg, 21%).

MS (ESI$^+$): m/z: 195 ([M+H]$^+$); $^1$H NMR (300 MHz, DMSO) δ 9.90 (brs, 1H), 7.47 (d, J=8.2 Hz, 2H), 6.83 (d, J=8.1 Hz, 2H), 3.69 (s, 3H), 2.83 (s, 2H), 2.37 (s, 2H).

Example 15

Synthesis of Compound WYQ-1

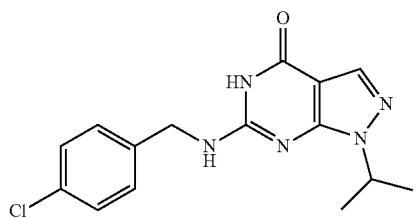

WYQ-1

Compound M-2 (64 mg, 0.3 mmol) obtained in Example 2, 4-chlorobenzylamine (51 mg, 0.36 mmol), triethylamine (40 mg, 0.4 mmol), and isopropanol (2 ml) were added into a reaction tube, and were reacted at 100° C. for 1 hour after the tube was sealed. After the reaction, the solvent was removed by rotatary evaporation. The reaction product was separated and purified via column chromatography (CH$_2$Cl$_2$:MeOH=20:1), and finally, light yellow solids were obtained (83 mg, 87%).

MS (ESI$^+$): m/z: 318 ([M+H]$^+$); $^1$H NMR (400 MHz, CDCl$_3$) δ 10.97 (brs, 1H), 7.52 (s, 1H), 7.34-7.27 (m, 4H), 6.89 (t, J=5.1 Hz, 1H), 4.85 (hept, J=6.7 Hz, 1H), 4.62 (d, J=5.2 Hz, 2H), 1.49 (d, J=6.7 Hz, 6H).

Example 16

Synthesis of Compound WYQ-2

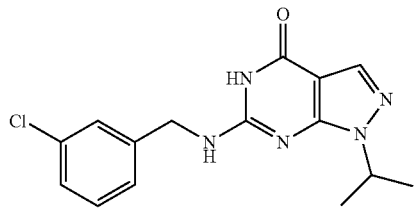

WYQ-2

The synthesis method was the same as that for the method for the synthesis of compound WYQ-1 in Example 15. Compound M-2 (64 mg, 0.3 mmol), 3-chlorobenzylamine (51 mg, 0.36 mmol), and isopropanol (6 ml) were reacted. The reaction product was separated and purified, and finally light yellow solids (90 mg, 94%) were obtained.

MS (ESI+): m/z: 318 ([M+H]+); 1H NMR (400 MHz, CDCl3) δ 7.54 (s, 1H), 7.41 (s, 1H), 7.27 (d, J=2.5 Hz, 2H), 6.85 (t, J=5.6 Hz, 1H), 4.92-4.81 (m, 1H), 4.63 (d, J=5.7 Hz, 2H), 1.49 (d, J=6.7 Hz, 6H).

Example 17

Synthesis of Compound WYQ-3

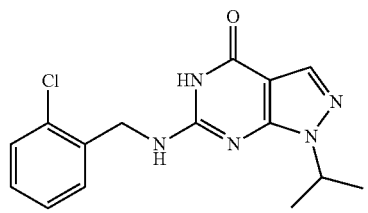

WYQ-3

The synthesis method was the same as that for the method for the synthesis of compound WYQ-1 in Example 15. Compound M-2 (64 mg, 0.3 mmol), 2-chlorobenzylamine (51 mg, 0.36 mmol), and isopropanol (3 ml) were reacted. The reaction product was separated and purified, and finally white solids (80 mg, 84%) were obtained.

MS (ESI+): m/z: 318 ([M+H]+); 1H NMR (400 MHz, CDCl3) δ 10.87 (brs, 1H), 7.53 (s, 1H), 7.53-7.49 (m, 1H), 7.41-7.36 (m, 1H), 7.25-7.21 (m, 2H), 7.08 (s, 1H), 4.89 (hept, J=6.7 Hz, 1H), 4.76 (d, J=5.8 Hz, 2H), 1.49 (d, J=6.7 Hz, 6H).

Example 18

Synthesis of Compound WYQ-4

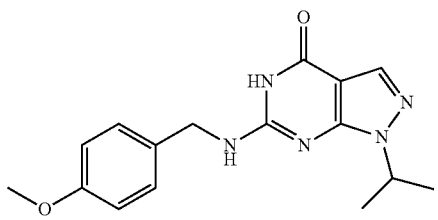

WYQ-4

The synthesis method was the same as that for the method for the synthesis of compound WYQ-1 in Example 15. Compound M-2 (64 mg, 0.3 mmol), 4-methoxybenzylamine (83 mg, 0.6 mmol), and isopropanol (1 ml) were reacted. The reaction product was separated and purified, and finally white solids (85 mg, 90%) were obtained.

MS (ESI+): m/z: 314 ([M+H]+); 1H NMR (400 MHz, CDCl3) δ 10.82 (brs, 1H), 7.33 (s, 1H), 7.33-7.30 (m, 2H), 6.92-6.85 (m, 3H), 4.89 (hept, J=6.7 Hz, 1H), 4.58 (d, J=5.2 Hz, 2H), 3.80 (s, 3H), 1.50 (d, J=6.7 Hz, 6H).

Example 19

Synthesis of Compound WYQ-5

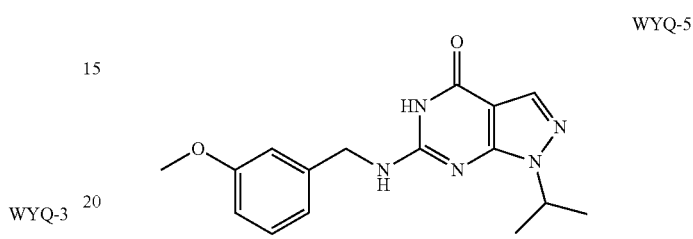

WYQ-5

The synthesis method was the same as that for the method for the synthesis of compound WYQ-1 in Example 15. Compound M-2 (64 mg, 0.3 mmol), 3-methoxybenzylamine (83 mg, 0.6 mmol), and isopropanol (2 ml) were reacted. The reaction product was separated and purified, and finally light yellow solids (87 mg, 92%) were obtained.

MS (ESI+): m/z: 314 ([M+H]+); 1H NMR (400 MHz, CDCl3) δ 10.91 (brs, 1H), 7.39 (s, 1H), 7.32-7.28 (m, 1H), 7.03-6.95 (m, 3H), 6.87 (dd, J=8.2, 2.2 Hz, 1H), 4.90 (hept, J=6.7 Hz, 1H), 4.65 (d, J=5.3 Hz, 2H), 3.79 (s, 3H), 1.51 (d, J=6.7 Hz, 6H).

Example 20

Synthesis of Compound WYQ-6

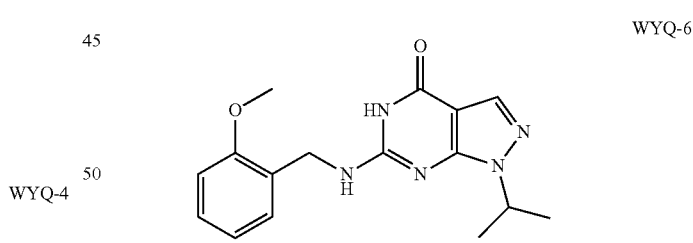

WYQ-6

The synthesis method was the same as that for the method for the synthesis of compound WYQ-1 in Example 15. Compound M-2 (64 mg, 0.3 mmol), 2-methoxybenzylamine (83 mg, 0.6 mmol), and isopropanol (2 ml) were reacted. The reaction product was separated and purified, and finally light yellow solids (89 mg, 95%) were obtained.

MS (ESI+): m/z: 314 ([M+H]+); 1H NMR (400 MHz, CDCl3) δ 10.98 (brs, 1H), 7.63 (s, 1H), 7.39 (dd, J=7.4, 1.6 Hz, 1H), 7.30-7.25 (m, 1H), 6.91 (ddd, J=8.2, 7.4, 3.4 Hz, 2H), 6.76 (s, 1H), 4.92 (hept, J=6.7 Hz, 1H), 4.63 (d, J=5.7 Hz, 2H), 3.83 (s, 3H), 1.52 (d, J=6.7 Hz, 6H).

Example 21

Synthesis of Compound WYQ-7

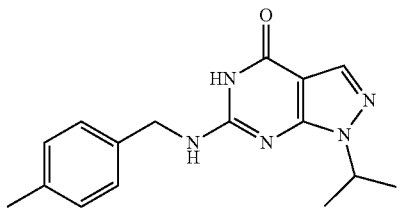

WYQ-7

The synthesis method was the same as that for the method for the synthesis of compound WYQ-1 in Example 15. Compound M-2 (64 mg, 0.3 mmol), 4-methylbenzylamine (73 mg, 0.6 mmol), and isopropanol (6 ml) were reacted. The reaction product was separated and purified, and finally light yellow solids (81 mg, 91%) were obtained.

MS (ESI$^-$): m/z: 296 ([M–H]$^-$); $^1$H NMR (400 MHz, DMSO) δ 10.84 (brs, 1H), 7.36-7.27 (m, 3H), 7.15 (d, J=7.3 Hz, 2H), 6.89 (s, 1H), 4.89 (dt, J=12.5, 6.1 Hz, 1H), 4.61 (s, 2H), 2.35 (s, 3H), 1.50 (d, J=6.5 Hz, 6H).

Example 22

Synthesis of Compound WYQ-8

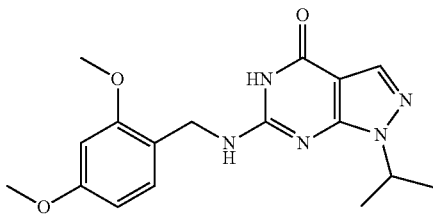

WYQ-8

The synthesis method was the same as that for the method for the synthesis of compound WYQ-1 in Example 15. Compound M-2 (64 mg, 0.3 mmol), 2,4-dimethoxybenzylamine (100 mg, 0.6 mmol), and isopropanol (0.6 ml) were reacted. The reaction product was separated and purified, and finally light yellow solids (86 mg, 83%) were obtained.

MS (ESI$^-$): m/z: 342 ([M–H]$^-$); $^1$H NMR (400 MHz, CDCl$_3$) δ 10.93 (brs, 1H), 7.63 (s, 1H), 7.30 (d, J=8.2 Hz, 1H), 6.70 (t, J=5.2 Hz, 1H), 6.48-6.40 (m, 2H), 4.92 (hept, J=6.7 Hz, 1H), 4.55 (d, J=5.7 Hz, 2H), 3.79 (d, J=1.9 Hz, 6H), 1.52 (d, J=6.7 Hz, 6H).

Example 23

Synthesis of Compound WYQ-9

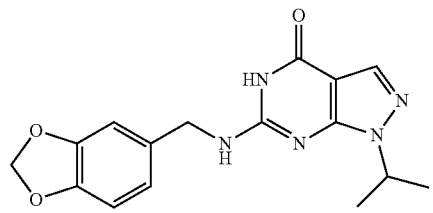

WYQ-9

The synthesis method was the same as that for the method for the synthesis of compound WYQ-1 in Example 15. Compound M-2 (64 mg, 0.3 mmol), 3,4-methylenedioxybenzylamine (68 mg, 0.45 mmol), and isopropanol (6 ml) were reacted. The reaction product was separated and purified, and finally light yellow solids (96 mg, 98%) were obtained.

MS (ESI$^-$): m/z: 326 ([M–H]$^-$); $^1$H NMR (400 MHz, CDCl$_3$) δ 10.90 (brs, 1H), 7.45 (s, 1H), 6.91 (brs, 1H), 6.89-6.83 (m, 2H), 6.77 (d, J=7.9 Hz, 1H), 5.94 (s, 2H), 4.89 (hept, J=6.7 Hz, 1H), 4.55 (d, J=4.4 Hz, 2H), 1.50 (d, J=6.7 Hz, 6H).

Example 24

Synthesis of Compound WYQ-10

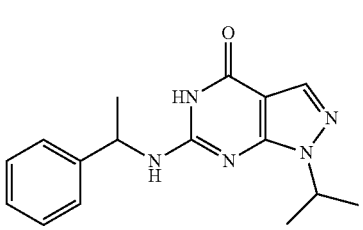

WYQ-10

The synthesis method was the same as that for the method for the synthesis of compound WYQ-1 in Example 15. Compound M-2 (64 mg, 0.3 mmol), α-methylbenzylamine (73 mg, 0.6 mmol), and isopropanol (5 ml) were reacted. The reaction product was separated and purified, and finally light yellow solids (83 mg, 93%) were obtained.

MS (ESI$^-$): m/z: 296 ([M–H]$^-$); $^1$H NMR (400 MHz, CDCl$_3$) δ 10.70 (brs, 1H), 7.59 (s, 1H), 7.45 (d, J=7.3 Hz, 2H), 7.36 (t, J=7.4 Hz, 2H), 7.31-7.27 (m, 1H), 7.21 (d, J=6.9 Hz, 1H), 5.26 (p, J=6.6 Hz, 1H), 4.91-4.79 (m, 1H), 1.67 (d, J=6.9 Hz, 3H), 1.49 (dd, J=21.9, 6.7 Hz, 6H).

Example 25

Synthesis of Compound WYQ-11

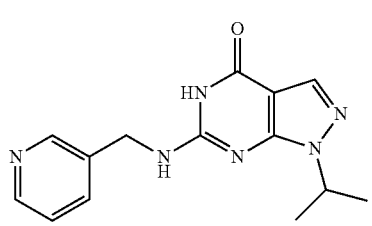

WYQ-11

The synthesis method was the same as that for the method for the synthesis of compound WYQ-1 in Example 15. Compound M-2 (64 mg, 0.3 mmol), 3-pyridinebenzylamine (65 mg, 0.6 mmol), and isopropanol (1 ml) were reacted. The reaction product was separated and purified, and finally white solids (80 mg, 92%) were obtained.

MS (ESI$^-$): m/z: 283 ([M–H]$^-$); $^1$H NMR (400 MHz, CDCl$_3$) δ 10.97 (brs, 1H), 8.65 (s, 1H), 8.49 (dd, J=4.7, 1.2 Hz, 1H), 7.70 (d, J=7.9 Hz, 1H), 7.55 (s, 1H), 7.23 (dd, J=7.8, 4.9 Hz, 1H), 6.92 (t, J=5.7 Hz, 1H), 4.88-4.76 (m, 1H), 4.63 (d, J=5.6 Hz, 2H), 1.45 (d, J=6.7 Hz, 6H).

Example 26

Synthesis of Compound WYQ-12

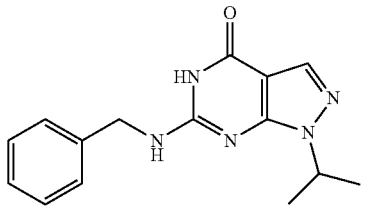

WYQ-12

The synthesis method was the same as that for the method for the synthesis of compound WYQ-1 in Example 15. Compound M-2 (64 mg, 0.3 mmol), α-methylbenzylamine (48 mg, 0.45 mmol), and isopropanol (3 ml) were reacted. The reaction product was separated and purified, and finally white solids (82 mg, 96%) were obtained.

MS (ESI$^-$): m/z: 282 ([M–H]$^-$); $^1$H NMR (400 MHz, CDCl$_3$) δ 10.93 (brs, 1H), 7.42-7.27 (m, 6H), 7.01 (d, J=8.3 Hz, 1H), 4.88 (hept, J=6.7 Hz, 1H), 4.66 (d, J=3.8 Hz, 2H), 1.49 (d, J=6.7 Hz, 6H).

Example 27

Synthesis of Compound WYQ-13

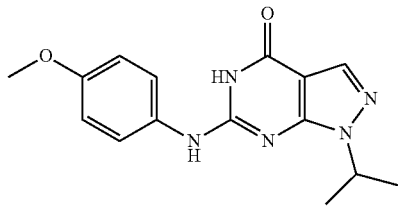

WYQ-13

The synthesis method was the same as that for the method for the synthesis of compound WYQ-1 in Example 15. Compound M-2 (64 mg, 0.3 mmol), 4-methoxybenzenamine (111 mg, 0.9 mmol), and isopropanol (2 ml) were reacted. The reaction product was separated and purified, and finally white solids (78 mg, 87%) were obtained.

MS (ESI$^-$): m/z: 298 ([M–H]$^-$); $^1$H NMR (400 MHz, CDCl$_3$) δ 10.61 (brs, 1H), 8.85 (brs, 1H), 7.88 (s, 1H), 7.58 (d, J=8.9 Hz, 2H), 6.94 (d, J=8.9 Hz, 2H), 4.95-4.86 (m, 1H), 3.83 (s, 3H), 1.53 (d, J=6.7 Hz, 6H).

Example 28

Synthesis of Compound WYQ-14

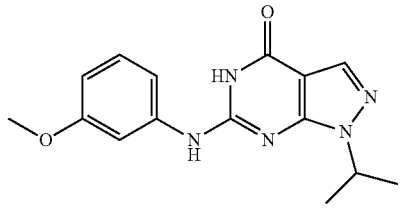

WYQ-14

The synthesis method was the same as that for the method for the synthesis of compound WYQ-1 in Example 15. Compound M-2 (64 mg, 0.3 mmol), 3-methoxybenzenamine (111 mg, 0.9 mmol), and isopropanol (2 ml) were reacted. The reaction product was separated and purified, and finally white solids (57 mg, 63%) were obtained.

MS (ESI$^-$): m/z: 298 ([M–H]$^-$); $^1$H NMR (400 MHz, DMSO) δ 10.35 (brs, 1H), 8.91 (brs, 1H), 7.85 (s, 1H), 7.53 (t, J=2.2 Hz, 1H), 7.25 (t, J=8.1 Hz, 1H), 7.05 (ddd, J=8.1, 2.0, 0.7 Hz, 1H), 6.64 (ddd, J=8.3, 2.5, 0.7 Hz, 1H), 4.80 (hept, J=6.7 Hz, 1H), 3.78 (s, 3H), 1.45 (d, J=6.7 Hz, 6H).

Example 29

Synthesis of Compound WYQ-15

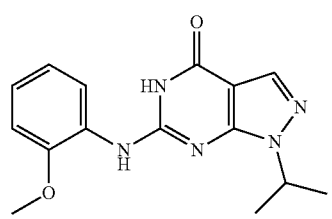

WYQ-15

The synthesis method was the same as that for the method for the synthesis of compound WYQ-1 in Example 15. Compound M-2 (64 mg, 0.3 mmol), 2-methoxybenzenamine (111 mg, 0.9 mmol), and isopropanol (4 ml) were reacted. The reaction product was separated and purified, and finally white solids (40 mg, 44%) were obtained.

MS (ESI$^-$): m/z: 298 ([M–H]$^-$); $^1$H NMR (400 MHz, DMSO) δ 11.06 (brs, 1H), 8.55 (brs, 1H), 8.46 (dd, J=7.8, 1.7 Hz, 1H), 7.85 (s, 1H), 7.14-6.96 (m, 3H), 4.91-4.74 (m, 1H), 3.91 (s, 3H), 1.45 (d, J=6.7 Hz, 6H).

Example 30

Synthesis of Compound WYQ-16

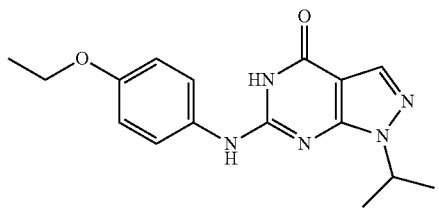

WYQ-16

The synthesis method was the same as that for the method for the synthesis of compound WYQ-1 in Example 15. Compound M-2 (64 mg, 0.3 mmol), 4-ethoxybenzenamine (123 mg, 0.9 mmol), and isopropanol (2 ml) were reacted. The reaction product was separated and purified, and finally white solids (89 mg, 95%) were obtained.

MS (ESI$^-$): m/z: 312 ([M–H]$^-$); $^1$H NMR (400 MHz, CDCl$_3$) δ 10.62 (brs, 1H), 8.80 (brs, 1H), 7.87 (s, 1H), 7.55 (d, J=9.0 Hz, 2H), 6.92 (d, J=9.0 Hz, 2H), 4.89 (hept, J=6.7 Hz, 1H), 4.05 (q, J=7.0 Hz, 2H), 1.52 (d, J=6.7 Hz, 6H), 1.43 (t, J=7.0 Hz, 3H).

Example 31

Synthesis of Compound WYQ-17

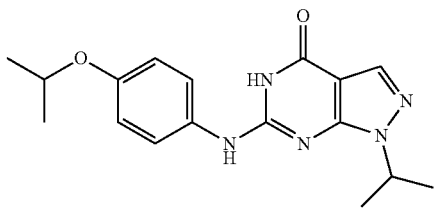

The synthesis method was the same as that for the method for the synthesis of compound WYQ-1 in Example 15. Compound M-2 (64 mg, 0.3 mmol), 4-isopropoxybenzenamine (136 mg, 0.9 mmol), and isopropanol (2 ml) were reacted. The reaction product was separated and purified, and finally white solids (87 mg, 89%) were obtained.

MS (ESI$^-$): m/z: 326 ([M–H]$^-$); $^1$H NMR (400 MHz, DMSO) δ 10.29 (brs, 1H), 8.67 (brs, 1H), 7.82 (s, 1H), 7.52 (d, J=9.0 Hz, 2H), 6.91 (d, J=9.0 Hz, 2H), 4.78 (hept, J=6.7 Hz, 1H), 4.55 (hept, J=6.0 Hz, 1H), 1.41 (d, J=6.7 Hz, 6H), 1.25 (d, J=6.0 Hz, 6H).

Example 32

Synthesis of Compound WYQ-18

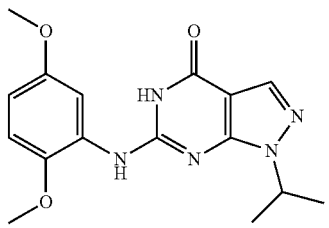

The synthesis method was the same as that for the method for the synthesis of compound WYQ-1 in Example 15. Compound M-2 (64 mg, 0.3 mmol), 2,5-dimethoxybenzenamine (138 mg, 0.9 mmol), and isopropanol (4 ml) were reacted. The reaction product was separated and purified, and finally white solids (30 mg, 30%) were obtained.

MS (ESI$^-$): m/z: 328 ([M–H]$^-$); $^1$H NMR (400 MHz, DMSO) δ 11.11 (brs, 1H), 8.59 (brs, 1H), 8.26 (d, J=3.0 Hz, 1H), 7.85 (s, 1H), 6.99 (d, J=8.9 Hz, 1H), 6.59 (dd, J=8.9, 3.1 Hz, 1H), 4.81 (hept, J=6.7 Hz, 1H), 3.85 (s, 3H), 3.76 (s, 3H), 1.47 (d, J=6.7 Hz, 6H).

Example 33

Synthesis of Compound WYQ-19

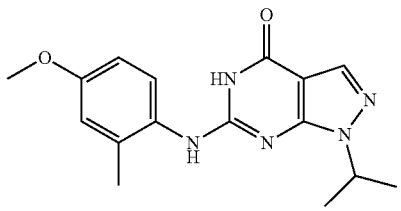

The synthesis method was the same as that for the method for the synthesis of compound WYQ-1 in Example 15. Compound M-2 (64 mg, 0.3 mmol), 2-methyl-4-methoxybenzenamine (123 mg, 0.9 mmol), and isopropanol (4 ml) were reacted. The reaction product was separated and purified, and finally white solids (77 mg, 80%) were obtained.

MS (ESI$^-$): m/z: 312 ([M–H]$^-$); $^1$H NMR (400 MHz, CDCl$_3$) δ 10.41 (brs, 1H), 7.80 (brs, 1H), 7.76 (s, 1H), 7.52 (d, J=8.4 Hz, 1H), 6.84-6.76 (m, 2H), 4.79 (hept, J=6.6 Hz, 1H), 3.82 (s, 3H), 2.32 (s, 3H), 1.46 (d, J=6.7 Hz, 6H).

Example 34

Synthesis of Compound WYQ-20

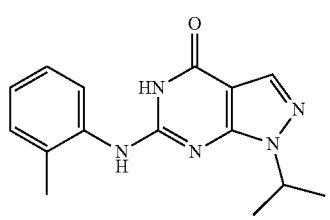

The synthesis method was the same as that for the method for the synthesis of compound WYQ-1 in Example 15. Compound M-2 (64 mg, 0.3 mmol), 2-methylbenzenamine (96 mg, 0.9 mmol), and isopropanol (3 ml) were reacted. The reaction product was separated and purified, and finally white solids (22 mg, 26%) were obtained.

MS (ESI$^-$): m/z: 282 ([M–H]$^-$); $^1$H NMR (400 MHz, DMSO) δ 10.76 (brs, 1H), 8.12 (brs, 1H), 7.97 (d, J=8.0 Hz, 1H), 7.83 (s, 1H), 7.24 (t, J=7.7 Hz, 2H), 7.09-7.03 (m, 1H), 4.70 (hept, J=6.7 Hz, 1H), 2.28 (s, 3H), 1.39 (d, J=6.7 Hz, 6H).

Example 35

Synthesis of Compound WYQ-21

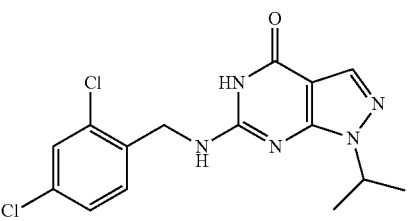

The synthesis method was the same as that for the method for the synthesis of compound WYQ-1 in Example 15. Compound M-2 (64 mg, 0.3 mmol), 2,4-dichlorobenzylamine (132 mg, 0.75 mmol), and isopropanol (3 ml) were reacted. The reaction product was separated and purified, and finally white solids (80 mg, 75%) were obtained.

MS (ESI$^-$): m/z: 350 ([M–H]$^-$); $^1$H NMR (400 MHz, CDCl$_3$) δ 11.03 (brs, 1H), 7.70 (s, 1H), 7.43 (d, J=8.2 Hz, 1H), 7.39 (d, J=2.0 Hz, 1H), 7.19 (dd, J=8.2, 1.9 Hz, 1H), 6.97 (brs, 1H), 4.86 (dt, J=13.3, 6.7 Hz, 1H), 4.70 (d, J=4.0 Hz, 2H), 1.49 (d, J=6.7 Hz, 6H).

Example 36

Synthesis of Compound WYQ-22

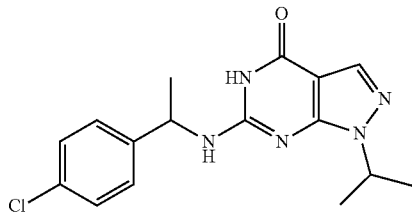

WYQ-22

The synthesis method was the same as that for the method for the synthesis of compound WYQ-1 in Example 15. Compound M-2 (64 mg, 0.3 mmol), 1-(4-chlorphenyl)ethylamine (93 mg, 0.6 mmol), and isopropanol (3 ml) were reacted. The reaction product was separated and purified, and finally white solids (69 mg, 69%) were obtained.

MS (ESI$^-$): m/z: 330 ([M−H]$^-$); $^1$H NMR (400 MHz, CDCl$_3$) δ 10.70 (brs, 1H), 7.65 (s, 1H), 7.34 (d, J=8.5 Hz, 2H), 7.30-7.26 (m, 2H), 7.14 (d, J=7.0 Hz, 1H), 5.18 (p, J=6.9 Hz, 1H), 4.77 (dt, J=13.5, 6.7 Hz, 1H), 1.61 (d, J=7.0 Hz, 3H), 1.48 (d, J=6.7 Hz, 3H), 1.41 (d, J=6.7 Hz, 3H).

Example 37

Synthesis of Compound WYQ-23

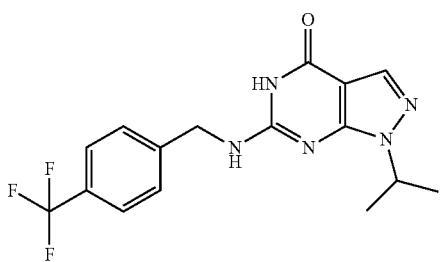

WYQ-23

The synthesis method was the same as that for the method for the synthesis of compound WYQ-1 in Example 15. Compound M-2 (64 mg, 0.3 mmol), 4-trifluoromethylbenzylamine (105 mg, 0.6 mmol), and isopropanol (1 ml) were reacted. The reaction product was separated and purified, and finally white solids (100 mg, 95%) were obtained.

MS (ESI$^-$): m/z: 350 ([M−H]$^-$); $^1$H NMR (500 MHz, DMSO) δ 10.62 (brs, 1H), 7.73 (s, 1H), 7.68 (d, J=8.1 Hz, 2H), 7.59 (d, J=8.1 Hz, 2H), 7.09 (t, J=5.6 Hz, 1H), 4.68 (dt, J=13.4, 6.7 Hz, 1H), 4.61 (d, J=5.8 Hz, 2H), 1.32 (d, J=6.7 Hz, 6H).

Example 38

Synthesis of Compound WYQ-24

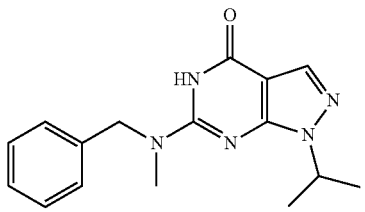

WYQ-24

The synthesis method was the same as that for the method for the synthesis of compound WYQ-1 in Example 15. Compound M-2 (64 mg, 0.3 mmol), N-methylbenzylamine (73 mg, 0.6 mmol), and isopropanol (2 ml) were reacted. The reaction product was separated and purified, and finally white solids (72 mg, 80%) were obtained.

MS (ESI$^-$): m/z: 296 ([M−H]$^-$); $^1$H NMR (500 MHz, DMSO) δ 10.66 (brs, 1H), 7.75 (s, 1H), 7.36-7.32 (m, 2H), 7.27 (dd, J=14.0, 7.2 Hz, 3H), 4.82 (s, 2H), 4.74 (dt, J=13.4, 6.7 Hz, 1H), 3.08 (s, 3H), 1.37 (d, J=6.7 Hz, 6H).

Example 39

Synthesis of Compound WYQ-25

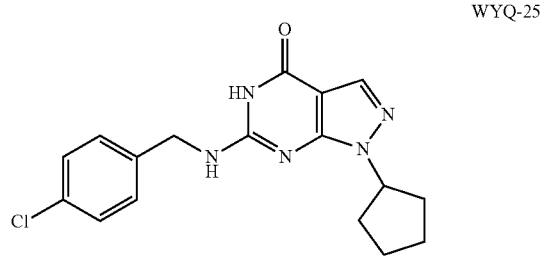 [SMILES: O=c1[nH]c(NCc2ccc(Cl)cc2)nc2c1cnn2C1CCCC1]

WYQ-25

Compound M-4 (71 mg, 0.3 mmol) obtained in Example 4, 4-chlorobenzylamine (85 mg, 0.6 mmol), triethylamine (40 mg, 0.4 mmol), and isopropanol (1 ml) were added into a reaction tube, and were reacted at 100° C. for 1 hour after the tube was sealed. After the reaction, the solvent was removed by rotatary evaporation. The reaction product was separated and purified via column chromatography (CH$_2$Cl$_2$:MeOH=20:1), and finally, white solids were obtained (81 mg, 79%).

MS (ESI$^-$): m/z: 342 ([M−H]$^-$); $^1$H NMR (400 MHz, CDCl$_3$) δ 11.00 (brs, 1H), 7.52 (s, 1H), 7.33-7.27 (m, 4H), 6.86 (brs, 1H), 4.99 (p, J=7.5 Hz, 1H), 4.62 (s, 2H), 2.06 (dd, J=12.7, 6.9 Hz, 4H), 1.99-1.87 (m, 2H), 1.74-1.62 (m, 2H).

Example 40

Synthesis of Compound WYQ-26

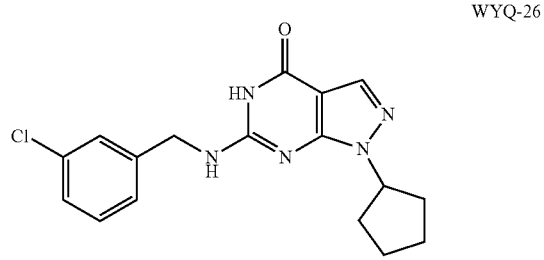 [SMILES: O=c1[nH]c(NCc2cccc(Cl)c2)nc2c1cnn2C1CCCC1]

WYQ-26

The synthesis method was the same as that for the method for the synthesis of compound WYQ-25 in Example 39. Compound M-4 (71 mg, 0.3 mmol), 3-chlorobenzylamine (85 mg, 0.6 mmol), and isopropanol (2 ml) were reacted. The reaction product was separated and purified, and finally white solids (84 mg, 82%) were obtained.

MS (ESI⁻): m/z: 342 ([M−H]⁻); ¹H NMR (400 MHz, CDCl₃) δ 11.02 (brs, 1H), 7.55 (s, 1H), 7.41 (s, 1H), 7.26 (s, 3H), 6.93 (s, 1H), 5.00 (p, J=7.1 Hz, 1H), 4.63 (s, 2H), 2.08 (s, 4H), 1.94 (s, 2H), 1.70 (d, J=4.3 Hz, 2H).

Example 41

Synthesis of Compound WYQ-27

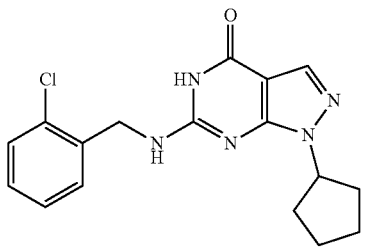
WYQ-27

The synthesis method was the same as that for the method for the synthesis of compound WYQ-25 in Example 39. Compound M-4 (71 mg, 0.3 mmol), 2-chlorobenzylamine (85 mg, 0.6 mmol), and isopropanol (6 ml) were reacted. The reaction product was separated and purified, and finally white solids (81 mg, 79%) were obtained.

MS (ESI⁻): m/z: 342 ([M−H]⁻); ¹H NMR (400 MHz, DMSO) δ 10.54 (brs, 1H), 7.73 (s, 1H), 7.49-7.43 (m, 2H), 7.35-7.26 (m, 2H), 7.03 (t, J=5.8 Hz, 1H), 4.88 (p, J=7.6 Hz, 1H), 4.60 (d, J=5.8 Hz, 2H), 1.97-1.83 (m, 4H), 1.82-1.73 (m, 2H), 1.59 (dt, J=8.4, 3.8 Hz, 2H).

Example 42

Synthesis of Compound WYQ-28

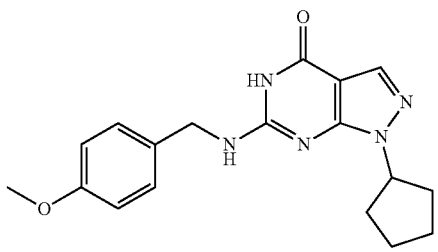
WYQ-28

The synthesis method was the same as that for the method for the synthesis of compound WYQ-25 in Example 39. Compound M-4 (71 mg, 0.3 mmol), 4-methoxybenzylamine (83 mg, 0.6 mmol), and isopropanol (4 ml) were reacted. The reaction product was separated and purified, and finally white solids (81 mg, 80%) were obtained.

MS (ESI⁻): m/z: 338 ([M−H]⁻); ¹H NMR (400 MHz, CDCl₃) δ 10.86 (brs, 1H), 7.36 (s, 1H), 7.31 (d, J=8.6 Hz, 2H), 6.89-6.85 (m, 2H), 5.02 (p, J=7.6 Hz, 1H), 4.58 (d, J=4.1 Hz, 2H), 3.80 (s, 3H), 2.13-2.02 (m, 4H), 2.00-1.90 (m, 2H), 1.69 (dd, J=10.3, 5.6 Hz, 2H).

Example 43

Synthesis of Compound WYQ-29

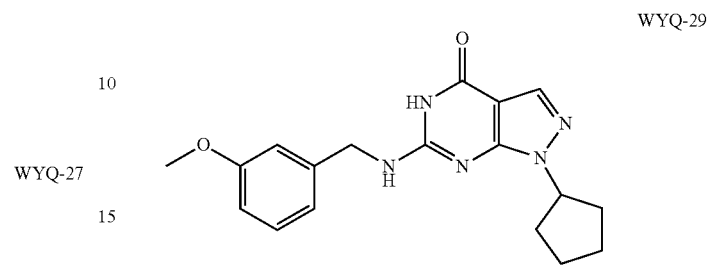
WYQ-29

The synthesis method was the same as that for the method for the synthesis of compound WYQ-25 in Example 39. Compound M-4 (71 mg, 0.3 mmol), 3-methoxybenzylamine (83 mg, 0.6 mmol), and isopropanol (3 ml) were reacted. The reaction product was separated and purified, and finally white solids (86 mg, 84%) were obtained.

MS (ESI⁻): m/z: 338 ([M−H]⁻); ¹H NMR (400 MHz, CDCl₃) δ 10.92 (brs, 1H), 7.39 (s, 1H), 7.29-7.24 (m, 1H), 6.99-6.94 (m, 2H), 6.84 (dd, J=8.2, 2.0 Hz, 1H), 5.01 (p, J=7.6 Hz, 1H), 4.63 (d, J=4.9 Hz, 2H), 3.76 (s, 3H), 2.11-2.02 (m, 4H), 1.98-1.88 (m, 2H), 1.74-1.64 (m, 2H).

Example 44

Synthesis of Compound WYQ-30

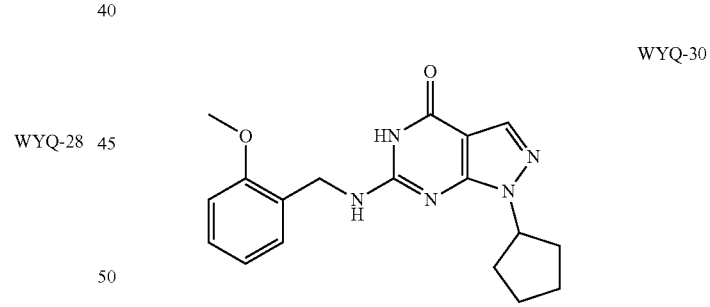
WYQ-30

The synthesis method was the same as that for the method for the synthesis of compound WYQ-25 in Example 39. Compound M-4 (71 mg, 0.3 mmol), 2-methoxybenzylamine (83 mg, 0.6 mmol), and isopropanol (2 ml) were reacted. The reaction product was separated and purified, and finally white solids (100 mg, 98%) were obtained.

MS (ESI⁻): m/z: 338 ([M−H]⁻); ¹H NMR (400 MHz, CDCl₃) δ 10.98 (brs, 1H), 7.60 (s, 1H), 7.39 (dd, J=7.4, 1.6 Hz, 1H), 7.30-7.24 (m, 1H), 6.94-6.86 (m, 2H), 6.76 (t, J=5.2 Hz, 1H), 5.05 (p, J=7.6 Hz, 1H), 4.64 (d, J=5.8 Hz, 2H), 3.83 (s, 3H), 2.14-2.06 (m, 4H), 1.99-1.91 (m, 2H), 1.72 (dd, J=7.3, 4.6 Hz, 2H).

Example 45

Synthesis of Compound WYQ-31

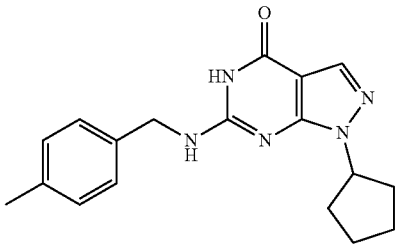

WYQ-31

The synthesis method was the same as that for the method for the synthesis of compound WYQ-25 in Example 39. Compound M-4 (71 mg, 0.3 mmol), 4-methylbenzylamine (109 mg, 0.9 mmol), and isopropanol (4 ml) were reacted. The reaction product was separated and purified, and finally white solids (70 mg, 72%) were obtained.

MS (ESI⁻): m/z: 322 ([M−H]⁻); $^1$H NMR (400 MHz, CDCl$_3$) δ 10.89 (brs, 1H), 7.35 (s, 1H), 7.28 (d, J=7.9 Hz, 2H), 7.14 (d, J=7.8 Hz, 2H), 6.89 (brs, 1H), 5.02 (p, J=7.5 Hz, 1H), 4.60 (s, 2H), 2.34 (s, 3H), 2.07 (dd, J=7.1, 5.5 Hz, 4H), 1.94 (dd, J=9.3, 5.7 Hz, 2H), 1.75-1.64 (m, 2H).

Example 46

Synthesis of Compound WYQ-32

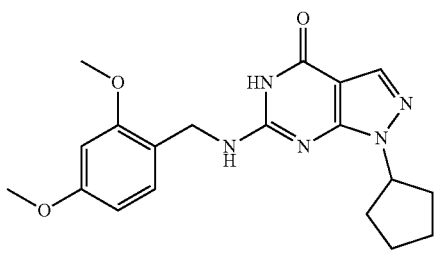

WYQ-32

The synthesis method was the same as that for the method for the synthesis of compound WYQ-25 in Example 39. Compound M-4 (71 mg, 0.3 mmol), 2,5-dimethoxybenzylamine (100 mg, 0.6 mmol), and isopropanol (3 ml) were reacted. The reaction product was separated and purified, and finally white solids (91 mg, 82%) were obtained.

MS (ESI⁻): m/z: 368 ([M−H]⁻); $^1$H NMR (400 MHz, CDCl$_3$) δ 10.93 (brs, 1H), 7.62 (s, 1H), 7.29 (d, J=8.2 Hz, 1H), 6.66 (brs, 1H), 6.47-6.40 (m, 2H), 5.06 (p, J=7.6 Hz, 1H), 4.55 (d, J=5.6 Hz, 2H), 3.79 (d, J=1.9 Hz, 6H), 2.14-2.07 (m, 4H), 2.01-1.93 (m, 2H), 1.76-1.68 (m, 2H).

Example 47

Synthesis of Compound WYQ-33

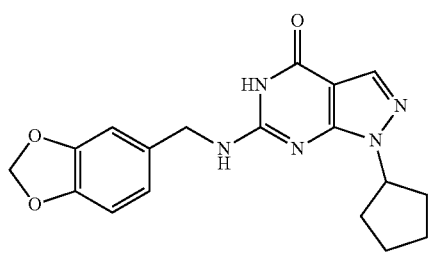

WYQ33

The synthesis method was the same as that for the method for the synthesis of compound WYQ-25 in Example 39. Compound M-4 (71 mg, 0.3 mmol), 3,4-methylenedioxybenzylamine (68 mg, 0.45 mmol), and isopropanol (5 ml) were reacted. The reaction product was separated and purified, and finally white solids (86 mg, 81%) were obtained.

MS (ESI⁻): m/z: 352 ([M−H]⁻); $^1$H NMR (400 MHz, CDCl$_3$) δ 10.85 (brs, 1H), 7.39 (s, 1H), 6.91-6.82 (m, 2H), 6.77 (d, J=7.8 Hz, 1H), 5.94 (s, 2H), 5.02 (p, J=7.6 Hz, 1H), 4.55 (d, J=3.0 Hz, 2H), 2.08 (dt, J=7.1, 6.3 Hz, 4H), 1.94 (dd, J=9.2, 5.9 Hz, 2H), 1.69 (dd, J=10.3, 5.6 Hz, 2H).

Example 48

Synthesis of Compound WYQ-34

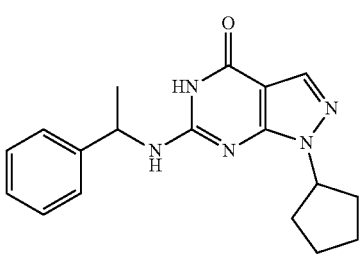

WYQ-34

The synthesis method was the same as that for the method for the synthesis of compound WYQ-25 in Example 39. Compound M-4 (71 mg, 0.3 mmol), α-methylbenzylamine (73 mg, 0.6 mmol), and isopropanol (0.6 ml) were reacted. The reaction product was separated and purified, and finally white solids (78 mg, 80%) were obtained.

MS (ESI⁻): m/z: 322 ([M−H]⁻); $^1$H NMR (400 MHz, CDCl$_3$) δ 10.70 (brs, 1H), 7.58 (s, 1H), 7.45-7.39 (m, 2H), 7.34 (t, J=7.4 Hz, 2H), 7.29-7.24 (m, 1H), 7.13 (d, J=7.0 Hz, 1H), 5.25 (p, J=6.8 Hz, 1H), 4.96 (p, J=7.6 Hz, 1H), 2.12-2.05 (m, 2H), 2.05-1.98 (m, 2H), 1.97-1.88 (m, 2H), 1.75-1.67 (m, 2H), 1.65 (d, J=6.9 Hz, 3H).

Example 49

Synthesis of Compound WYQ-35

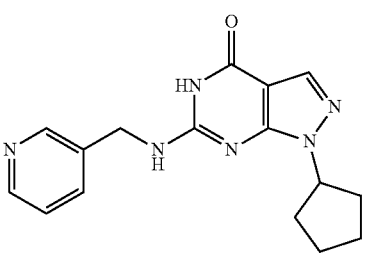

WYQ-35

The synthesis method was the same as that for the method for the synthesis of compound WYQ-25 in Example 39. Compound M-4 (71 mg, 0.3 mmol), 3-pyridinebenzylamine (65 mg, 0.6 mmol), and isopropanol (0.8 ml) were reacted. The reaction product was separated and purified, and finally white solids (77 mg, 83%) were obtained.

MS (ESI⁻): m/z: 309 ([M−H]⁻); ¹H NMR (400 MHz, CDCl₃) δ 11.02 (brs, 1H), 8.69 (s, 1H), 8.54 (d, J=3.8 Hz, 1H), 7.74 (d, J=7.7 Hz, 1H), 7.58 (s, 1H), 7.28 (d, J=7.0 Hz, 1H), 6.92 (t, J=5.5 Hz, 1H), 5.00 (p, J=7.4 Hz, 1H), 4.68 (d, J=5.3 Hz, 2H), 2.07 (d, J=3.8 Hz, 4H), 1.94 (s, 2H), 1.70 (d, J=4.5 Hz, 2H).

Example 50

Synthesis of Compound WYQ-36

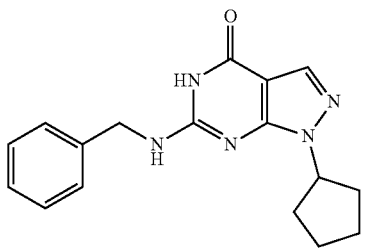

WYQ-36

The synthesis method was the same as that for the method for the synthesis of compound WYQ-25 in Example 39. Compound M-4 (71 mg, 0.3 mmol), benzylamine (64 mg, 0.6 mmol), and isopropanol (1 ml) were reacted. The reaction product was separated and purified, and finally white solids (82 mg, 88%) were obtained.

MS (ESI⁻): m/z: 308 ([M−H]⁻); ¹H NMR (400 MHz, CDCl₃) δ 10.93 (brs, 1H), 7.42-7.27 (m, 6H), 5.01 (p, J=7.6 Hz, 1H), 4.66 (d, J=4.9 Hz, 2H), 2.13-2.01 (m, 4H), 1.99-1.88 (m, 2H), 1.74-1.63 (m, 2H).

Example 51

Synthesis of Compound WYQ-37

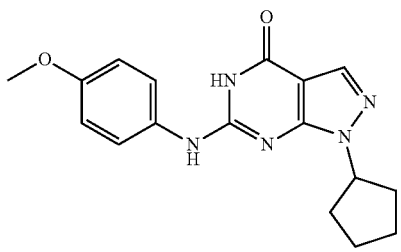

WYQ-37

The synthesis method was the same as that for the method for the synthesis of compound WYQ-25 in Example 39. Compound M-4 (71 mg, 0.3 mmol), 4-methoxybenzenamine (111 mg, 0.9 mmol), and isopropanol (2 ml) were reacted. The reaction product was separated and purified, and finally white solids (65 mg, 67%) were obtained.

MS (ESI⁻): m/z: 324 ([M−H]⁻); ¹H NMR (400 MHz, DMSO) δ 10.30 (brs, 1H), 8.69 (brs, 1H), 7.82 (s, 1H), 7.55 (d, J=9.0 Hz, 2H), 6.95 (d, J=9.0 Hz, 2H), 5.00-4.89 (m, 1H), 3.75 (s, 3H), 2.10-1.91 (m, 4H), 1.90-1.79 (m, 2H), 1.66 (dt, J=8.8, 4.0 Hz, 2H).

Example 52

Synthesis of Compound WYQ-38

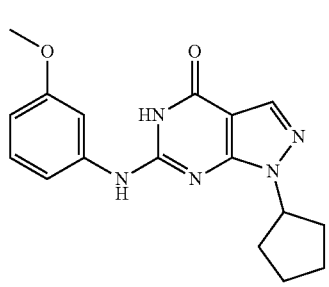

WYQ-38

The synthesis method was the same as that for the method for the synthesis of compound WYQ-25 in Example 39. Compound M-4 (71 mg, 0.3 mmol), 3-methoxybenzenamine (111 mg, 0.9 mmol), and isopropanol (1 ml) were reacted. The reaction product was separated and purified, and finally white solids (40 mg, 41%) were obtained.

MS (ESI⁻): m/z: 324 ([M−H]⁻); ¹H NMR (400 MHz, CDCl₃) δ 10.75 (brs, 1H), 8.98 (brs, 1H), 7.92 (s, 1H), 7.55 (t, J=2.1 Hz, 1H), 7.30-7.25 (m, 1H), 7.12 (dd, J=8.0, 1.2 Hz, 1H), 6.69 (dd, J=8.1, 2.1 Hz, 1H), 5.05 (p, J=7.5 Hz, 1H), 3.84 (s, 3H), 2.13 (dt, J=7.1, 3.7 Hz, 4H), 1.96 (dd, J=10.1, 5.9 Hz, 2H), 1.77-1.65 (m, 2H).

Example 53

Synthesis of Compound WYQ-39

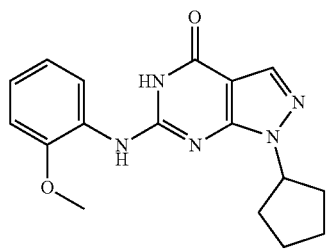

WYQ-39

The synthesis method was the same as that for the method for the synthesis of compound WYQ-25 in Example 39. Compound M-4 (71 mg, 0.3 mmol), 2-methoxybenzenamine (111 mg, 0.9 mmol), and isopropanol (1 ml) were reacted. The reaction product was separated and purified, and finally white solids (40 mg, 41%) were obtained.

MS (ESI⁻): m/z: 324 ([M−H]⁻); ¹H NMR (400 MHz, DMSO) δ 11.06 (brs, 1H), 8.55 br (s, 1H), 8.46 (dd, J=7.8, 1.7 Hz, 1H), 7.85 (s, 1H), 7.12-6.97 (m, 3H), 5.04-4.94 (m, 1H), 3.90 (s, 3H), 2.14-1.93 (m, 4H), 1.93-1.81 (m, 2H), 1.73-1.60 (m, 2H).

Example 54

Synthesis of Compound WYQ-40

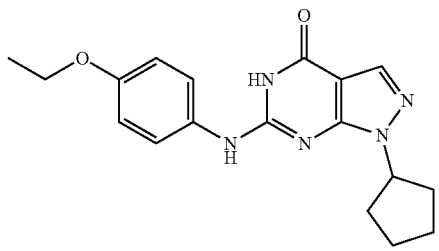

WYQ-40

The synthesis method was the same as that for the method for the synthesis of compound WYQ-25 in Example 39. Compound M-4 (71 mg, 0.3 mmol), 4-ethoxybenzenamine (123 mg, 0.9 mmol), and isopropanol (3 ml) were reacted. The reaction product was separated and purified, and finally white solids (70 mg, 70%) were obtained.

MS (ESI$^-$): m/z: 338 ([M−H]$^-$); $^1$H NMR (400 MHz, CDCl$_3$) δ 10.56 (brs, 1H), 8.75 (brs, 1H), 7.85 (s, 1H), 7.56-7.50 (m, 2H), 6.95-6.89 (m, 2H), 5.01 (p, J=7.5 Hz, 1H), 4.05 (q, J=7.0 Hz, 2H), 2.11 (ddd, J=7.4, 6.4, 2.6 Hz, 4H), 2.00-1.89 (m, 2H), 1.76-1.66 (m, 2H), 1.43 (t, J=7.0 Hz, 3H).

Example 55

Synthesis of Compound WYQ-41

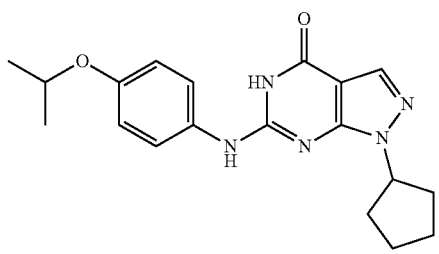

WYQ-41

The synthesis method was the same as that for the method for the synthesis of compound WYQ-25 in Example 39. Compound M-4 (71 mg, 0.3 mmol), 4-isopropoxybenzenamine (136 mg, 0.9 mmol), and isopropanol (3 ml) were reacted. The reaction product was separated and purified, and finally white solids (75 mg, 71%) were obtained.

MS (ESI$^-$): m/z: 352 ([M−H]$^-$); $^1$H NMR (400 MHz, CDCl$_3$) δ 10.54 (brs, 1H), 8.71 (brs, 1H), 7.87 (s, 1H), 7.54 (d, J=8.7 Hz, 2H), 6.92 (d, J=8.7 Hz, 2H), 5.02 (p, J=7.4 Hz, 1H), 4.53 (hept, J=6.0 Hz, 1H), 2.12 (d, J=5.4 Hz, 4H), 1.94 (d, J=6.4 Hz, 2H), 1.76-1.64 (m, 2H), 1.36 (d, J=6.0 Hz, 6H).

Example 56

Synthesis of Compound WYQ-42

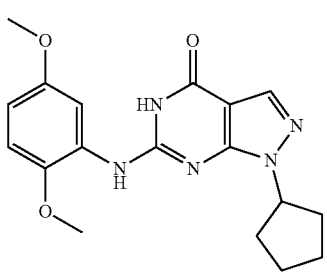

WYQ-42

The synthesis method was the same as that for the method for the synthesis of compound WYQ-25 in Example 39. Compound M-4 (71 mg, 0.3 mmol), 2,5-dimethoxybenzenamine (138 mg, 0.9 mmol), and isopropanol (4 ml) were reacted. The reaction product was separated and purified, and finally white solids (27 mg, 27%) were obtained.

MS (ESI$^-$): m/z: 354 ([M−H]$^-$); $^1$H NMR (400 MHz, DMSO) δ 11.09 (brs, 1H), 8.58 (brs, 1H), 8.27 (d, J=3.0 Hz, 1H), 7.84 (s, 1H), 6.98 (d, J=8.9 Hz, 1H), 6.58 (dd, J=8.9, 3.1 Hz, 1H), 4.97 (p, J=7.3 Hz, 1H), 3.84 (s, 3H), 3.75 (s, 3H), 2.12-1.96 (m, 4H), 1.91-1.80 (m, 2H), 1.70-1.60 (m, 2H).

Example 57

Synthesis of Compound WYQ-43

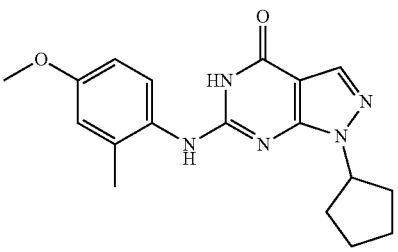

WYQ-43

The synthesis method was the same as that for the method for the synthesis of compound WYQ-25 in Example 39. Compound M-4 (71 mg, 0.3 mmol), 2-methyl-4-methoxybenzenamine (123 mg, 0.9 mmol), and isopropanol (4 ml) were reacted. The reaction product was separated and purified, and finally white solids (77 mg, 75%) were obtained.

MS (ESI$^-$): m/z: 338 ([M−H]$^-$); $^1$H NMR (500 MHz, DMSO) δ 10.55 (brs, 1H), 8.04 (brs, 1H), 7.78 (s, 1H), 7.62 (d, J=8.7 Hz, 1H), 6.84 (d, J=2.8 Hz, 1H), 6.80 (dd, J=8.8, 2.8 Hz, 1H), 4.80 (dt, J=14.6, 7.4 Hz, 1H), 3.27 (s, 3H), 2.22 (s, 3H), 1.99-1.88 (m, 4H), 1.79 (dd, J=12.8, 9.6 Hz, 2H), 1.63-1.53 (m, 2H).

Example 58

Synthesis of Compound WYQ-44

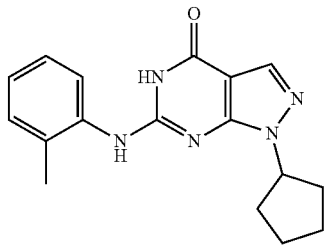

WYQ-44

The synthesis method was the same as that for the method for the synthesis of compound WYQ-25 in Example 39. Compound M-4 (71 mg, 0.3 mmol), 2-methylbenzenamine (96 mg, 0.9 mmol), and isopropanol (5 ml) were reacted. The reaction product was separated and purified, and finally white solids (14 mg, 15%) were obtained.

MS (ESI⁻): m/z: 308 ([M−H]⁻); $^1$H NMR (400 MHz, DMSO) δ 10.79 (brs, 1H), 8.15 (brs, 1H), 7.95 (d, J=7.9 Hz, 1H), 7.82 (s, 1H), 7.23 (t, J=7.8 Hz, 2H), 7.06 (dd, J=11.1, 3.7 Hz, 1H), 4.90-4.79 (m, 1H), 2.26 (s, 3H), 1.96 (dtd, J=18.8, 12.6, 6.1 Hz, 4H), 1.79 (dd, J=9.0, 5.7 Hz, 2H), 1.59 (dd, J=9.8, 5.3 Hz, 2H).

Example 59

Synthesis of Compound WYQ-45

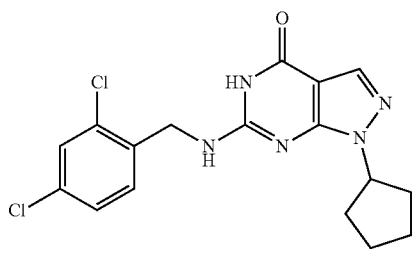

WYQ-45

The synthesis method was the same as that for the method for the synthesis of compound WYQ-25 in Example 39. Compound M-4 (71 mg, 0.3 mmol), 2,4-dichlorobenzylamine (106 mg, 0.6 mmol), and isopropanol (4 ml) were reacted. The reaction product was separated and purified, and finally white solids (75 mg, 66%) were obtained.

MS (ESI⁻): m/z: 376 ([M−H]⁻); $^1$H NMR (400 MHz, DMSO) δ 10.61 (brs, 1H), 7.73 (s, 1H), 7.62 (d, J=2.1 Hz, 1H), 7.42 (dt, J=8.3, 5.2 Hz, 2H), 7.08 (t, J=5.7 Hz, 1H), 4.93-4.77 (m, 1H), 4.57 (d, J=5.8 Hz, 2H), 1.98-1.71 (m, 6H), 1.65-1.54 (m, 2H).

Example 60

Synthesis of Compound WYQ-46

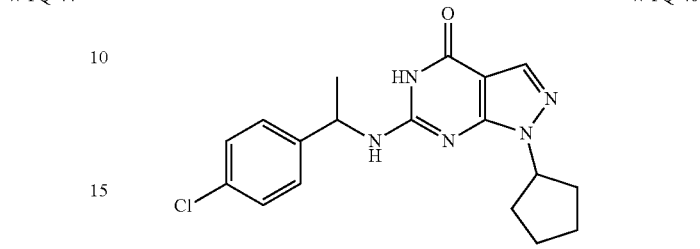

WYQ-46

The synthesis method was the same as that for the method for the synthesis of compound WYQ-25 in Example 39. Compound M-4 (71 mg, 0.3 mmol), 1-(4-chlorphenyl)ethylamine (93 mg, 0.6 mmol), and isopropanol (5 ml) were reacted. The reaction product was separated and purified, and finally white solids (49 mg, 46%) were obtained.

MS (ESI⁻): m/z: 356 ([M−H]⁻); $^1$H NMR (400 MHz, CDCl₃) δ 10.72 (brs, 1H), 7.64 (s, 1H), 7.36-7.32 (m, 2H), 7.30-7.26 (m, 2H), 7.07 (d, J=7.1 Hz, 1H), 5.18 (p, J=6.9 Hz, 1H), 4.90 (p, J=7.5 Hz, 1H), 2.09-2.03 (m, 2H), 1.97 (dd, J=8.6, 5.2 Hz, 2H), 1.90 (ddd, J=14.2, 9.4, 4.1 Hz, 2H), 1.73-1.65 (m, 2H), 1.61 (d, J=7.0 Hz, 3H).

Example 61

Synthesis of Compound WYQ-47

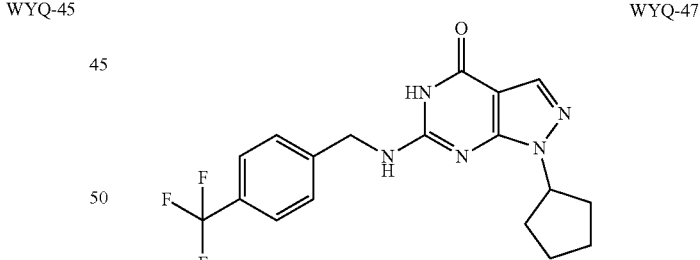

WYQ-47

The synthesis method was the same as that for the method for the synthesis of compound WYQ-25 in Example 39. Compound M-4 (71 mg, 0.3 mmol), 4-trifluoromethylbenzylamine (105 mg, 0.6 mmol), and isopropanol (5 ml) were reacted. The reaction product was separated and purified, and finally white solids (92 mg, 81%) were obtained.

MS (ESI⁻): m/z: 376 ([M−H]⁻); $^1$H NMR (400 MHz, DMSO) δ 10.65 (brs, 1H), 7.73 (s, 1H), 7.69 (d, J=8.1 Hz, 2H), 7.58 (d, J=8.0 Hz, 2H), 7.10 (t, J=5.8 Hz, 1H), 4.89-4.79 (m, 1H), 4.61 (d, J=5.8 Hz, 2H), 1.96-1.73 (m, 6H), 1.63-1.53 (m, 2H).

Example 62

Synthesis of Compound WYQ-48

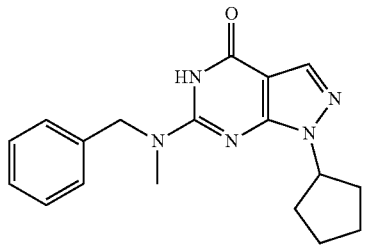

WYQ-48

The synthesis method was the same as that for the method for the synthesis of compound WYQ-25 in Example 39. Compound M-4 (71 mg, 0.3 mmol), N-methylbenzylamine (73 mg, 0.6 mmol), and isopropanol (3 ml) were reacted. The reaction product was separated and purified, and finally white solids (45 mg, 46%) were obtained.

MS (ESI⁻): m/z: 322 ([M–H]⁻); $^1$H NMR (400 MHz, DMSO) δ 7.76 (s, 1H), 7.39-7.23 (m, 5H), 4.96-4.86 (m, 1H), 4.82 (s, 2H), 3.08 (s, 3H), 2.03-1.76 (m, 6H), 1.60 (dd, J=9.9, 5.3 Hz, 2H).

Example 63

Synthesis of Compound WYQ-49

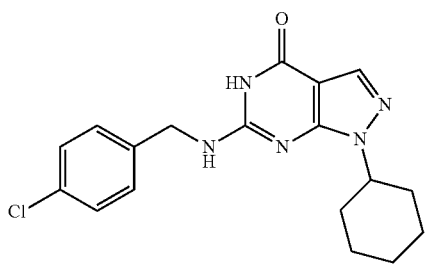

WYQ-49

Compound M-6 (76 mg, 0.3 mmol) obtained in Example 6, 4-chlorobenzylamine (85 mg, 0.6 mmol), triethylamine (40 mg, 0.4 mmol), and isopropanol (6 ml) were added into a reaction tube, and were reacted at 100° C. for 1 hour after the tube was sealed. After the reaction, the solvent was removed by rotatary evaporation. The reaction product was separated and purified via column chromatography (CH₂Cl₂:MeOH=20:1), and finally white solids were obtained (76 mg, 71%).

MS (ESI⁻): m/z: 356 ([M–H]⁻); $^1$H NMR (400 MHz, CDCl₃) δ 11.04 (brs, 1H), 7.52 (s, 1H), 7.31 (q, J=8.5 Hz, 4H), 6.87 (brs, 1H), 4.62 (d, J=4.4 Hz, 2H), 4.46-4.36 (m, 1H), 1.97-1.69 (m, 7H), 1.49-1.27 (m, 3H).

Example 64

Synthesis of Compound WYQ-50

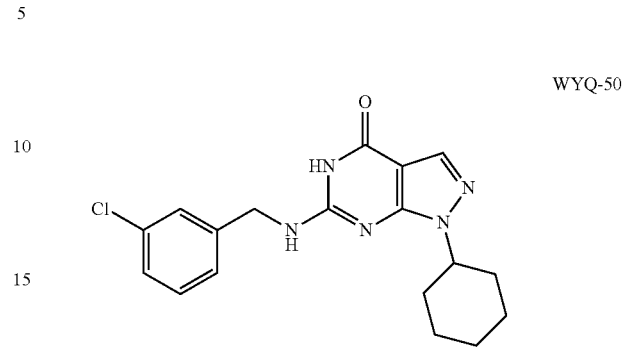

WYQ-50

The synthesis method was the same as that for the method for the synthesis of compound WYQ-49 in Example 63. Compound M-6 (76 mg, 0.3 mmol), 3-chlorobenzylamine (85 mg, 0.6 mmol), and isopropanol (1 ml) were reacted. The reaction product was separated and purified, and finally white solids (82 mg, 77%) were obtained.

MS (ESI⁻): m/z: 356 ([M–H]⁻); $^1$H NMR (400 MHz, DMSO) δ 10.61 (brs, 1H), 7.71 (s, 1H), 7.47 (s, 1H), 7.37-7.32 (m, 2H), 7.32-7.26 (m, 1H), 7.08 (t, J=5.8 Hz, 1H), 4.48 (d, J=5.9 Hz, 2H), 4.35-4.25 (m, 1H), 1.83-1.63 (m, 7H), 1.41-1.16 (m, 3H).

Example 65

Synthesis of Compound WYQ-51

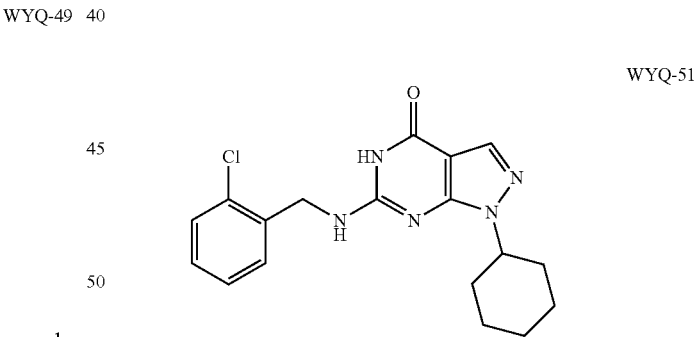

WYQ-51

The synthesis method was the same as that for the method for the synthesis of compound WYQ-49 in Example 63. Compound M-6 (76 mg, 0.3 mmol), 2-chlorobenzylamine (85 mg, 0.6 mmol), and isopropanol (6 ml) were reacted. The reaction product was separated and purified, and finally white solids (75 mg, 70%) were obtained.

MS (ESI⁻): m/z: 356 ([M–H]⁻); $^1$H NMR (400 MHz, DMSO) δ 10.15 (brs, 1H), 7.70 (s, 1H), 7.52-7.41 (m, 2H), 7.32-7.24 (m, 2H), 7.09 (t, J=5.7 Hz, 1H), 4.59 (d, J=5.8 Hz, 2H), 4.36-4.21 (m, 1H), 1.81-1.61 (m, 7H), 1.41-1.14 (m, 3H).

Example 66

Synthesis of Compound WYQ-52

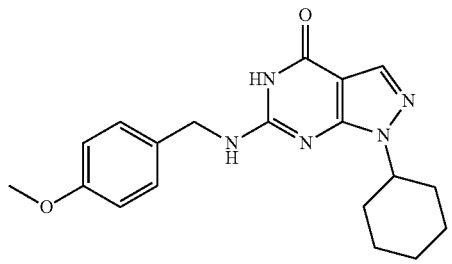

WYQ-52

The synthesis method was the same as that for the method for the synthesis of compound WYQ-49 in Example 63. Compound M-6 (76 mg, 0.3 mmol), 4-methoxybenzylamine (50 mg, 0.36 mmol), and isopropanol (0.6 ml) were reacted. The reaction product was separated and purified, and finally white solids (76 mg, 72%) were obtained.

MS (ESI−): m/z: 352 ([M−H]−); $^1$H NMR (400 MHz, CDCl$_3$) δ 10.95 (brs, 1H), 7.44 (s, 1H), 7.32 (d, J=8.5 Hz, 2H), 6.87 (d, J=8.5 Hz, 2H), 4.58 (d, J=3.1 Hz, 2H), 4.51-4.40 (m, 1H), 3.80 (s, 3H), 2.02-1.68 (m, 7H), 1.49-1.25 (m, 3H).

Example 67

Synthesis of Compound WYQ-53

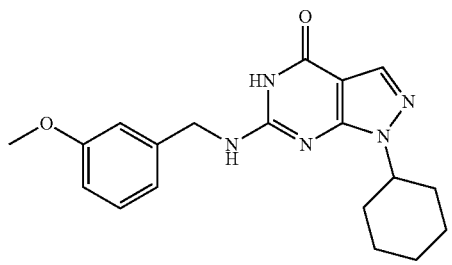

WYQ-53

The synthesis method was the same as that for the method for the synthesis of compound WYQ-49 in Example 63. Compound M-6 (76 mg, 0.3 mmol), 3-methoxybenzylamine (50 mg, 0.36 mmol), and isopropanol (2 ml) were reacted. The reaction product was separated and purified, and finally white solids (78 mg, 74%) were obtained.

MS (ESI−): m/z: 352 ([M−H]−); $^1$H NMR (400 MHz, DMSO) δ 10.46 (brs, 1H), 7.72 (s, 1H), 7.24 (dd, J=11.6, 4.3 Hz, 1H), 6.97 (d, J=1.4 Hz, 2H), 6.85-6.79 (m, 1H), 4.47 (d, J=5.7 Hz, 2H), 4.33 (ddd, J=15.2, 10.0, 5.2 Hz, 1H), 3.73 (s, 3H), 1.88-1.60 (m, 7H), 1.45-1.13 (m, 3H).

Example 68

Synthesis of Compound WYQ-54

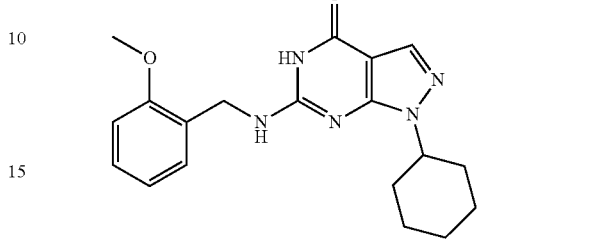

WYQ-54

The synthesis method was the same as that for the method for the synthesis of compound WYQ-49 in Example 63. Compound M-6 (76 mg, 0.3 mmol), 2-methoxybenzylamine (50 mg, 0.36 mmol), and isopropanol (2 ml) were reacted. The reaction product was separated and purified, and finally white solids (77 mg, 73%) were obtained.

MS (ESI−): m/z: 352 ([M−H]−); $^1$H NMR (400 MHz, CDCl$_3$) δ 10.95 (brs, 1H), 7.62 (s, 1H), 7.41 (dd, J=7.4, 1.6 Hz, 1H), 7.30-7.24 (m, 1H), 6.90 (ddd, J=8.2, 6.7, 2.9 Hz, 2H), 4.63 (d, J=5.7 Hz, 2H), 4.55-4.43 (m, 1H), 3.83 (s, 3H), 2.03-1.69 (m, 7H), 1.54-1.28 (m, 3H).

Example 69

Synthesis of Compound WYQ-55

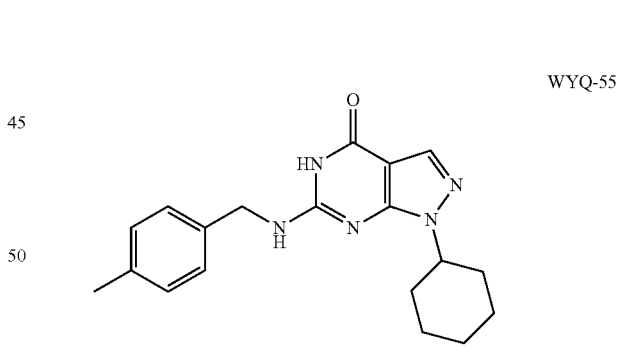

WYQ-55

The synthesis method was the same as that for the method for the synthesis of compound WYQ-49 in Example 63. Compound M-6 (76 mg, 0.3 mmol), 4-methylbenzylamine (73 mg, 0.6 mmol), and isopropanol (1 ml) were reacted. The reaction product was separated and purified, and finally white solids (78 mg, 77%) were obtained.

MS (ESI-): m/z: 336 ([M−H]-); 1H NMR (400 MHz, CDCl3) δ 10.86 (s, 1H), 7.34 (s, 1H), 7.29 (d, J=7.9 Hz, 2H), 7.14 (d, J=7.9 Hz, 2H), 4.60 (d, J=4.8 Hz, 2H), 4.52-4.38 (m, 1H), 2.34 (s, 3H), 2.02-1.68 (m, 7H), 1.48-1.26 (m, 3H).

Example 70

Synthesis of Compound WYQ-56

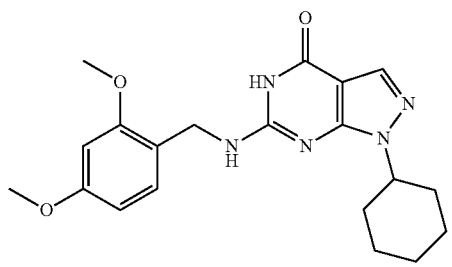

The synthesis method was the same as that for the method for the synthesis of compound WYQ-49 in Example 63. Compound M-6 (76 mg, 0.3 mmol), 2,5-dimethoxybenzylamine (100 mg, 0.6 mmol), and isopropanol (4 ml) were reacted. The reaction product was separated and purified, and finally white solids (85 mg, 74%) were obtained.

MS (ESI⁻): m/z: 382 ([M−H]⁻); $^1$H NMR (400 MHz, CDCl$_3$) δ 10.89 (brs, 1H), 7.62 (s, 1H), 7.31 (d, J=8.2 Hz, 1H), 6.81 (s, 1H), 6.51-6.34 (m, 2H), 4.55 (d, J=5.2 Hz, 2H), 4.48 (dd, J=14.6, 7.0 Hz, 1H), 3.78 (s, 6H), 2.01-1.73 (m, 7H), 1.37 (dd, J=44.9, 32.2 Hz, 3H).

Example 71

Synthesis of Compound WYQ-57

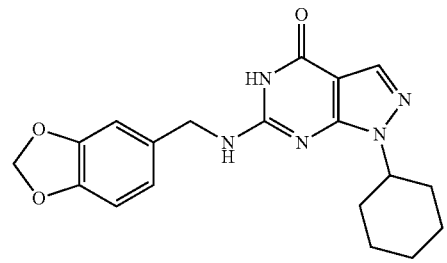

The synthesis method was the same as that for the method for the synthesis of compound WYQ-49 in Example 63. Compound M-6 (76 mg, 0.3 mmol), 3,4-methylenedioxybenzylamine (68 mg, 0.45 mmol), and isopropanol (2 ml) were reacted. The reaction product was separated and purified, and finally white solids (82 mg, 74%) were obtained.

MS (ESI⁻): m/z: 366 ([M−H]⁻); $^1$H NMR (400 MHz, DMSO) δ 10.44 (brs, 1H), 7.71 (s, 1H), 6.98 (d, J=1.1 Hz, 1H), 6.93-6.82 (m, 2H), 6.85 (brs, 1H), 5.97 (s, 2H), 4.39 (d, J=5.7 Hz, 2H), 4.37-4.28 (m, 1H), 1.86-1.62 (m, 7H), 1.45-1.17 (m, 3H).

Example 72

Synthesis of Compound WYQ-58

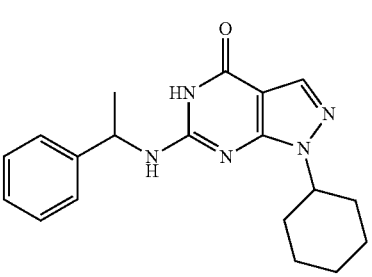

The synthesis method was the same as that for the method for the synthesis of compound WYQ-49 in Example 63. Compound M-6 (76 mg, 0.3 mmol), α-methylbenzylamine (73 mg, 0.6 mmol), and isopropanol (3 ml) were reacted. The reaction product was separated and purified, and finally white solids (72 mg, 71%) were obtained.

MS (ESI⁻): m/z: 336 ([M−H]⁻); $^1$H NMR (400 MHz, CDCl$_3$) δ 10.70 (brs, 1H), 7.60 (s, 1H), 7.47-7.41 (m, 2H), 7.35 (dd, J=10.2, 4.7 Hz, 2H), 7.28-7.23 (m, 1H), 7.21 (d, J=6.7 Hz, 1H), 5.21 (p, J=6.8 Hz, 1H), 4.44-4.32 (m, 1H), 2.01-1.74 (m, 7H), 1.66 (d, J=6.9 Hz, 3H), 1.50-1.28 (m, 3H).

Example 73

Synthesis of Compound WYQ-59

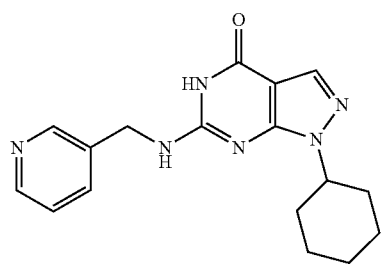

The synthesis method was the same as that for the method for the synthesis of compound WYQ-49 in Example 63. Compound M-6 (76 mg, 0.3 mmol), 3-pyridinebenzylamine (65 mg, 0.6 mmol), and isopropanol (6 ml) were reacted. The reaction product was separated and purified, and finally white solids (61 mg, 63%) were obtained.

MS (ESI⁻): m/z: 323 ([M−H]⁻); $^1$H NMR (400 MHz, CDCl$_3$) δ 11.04 (brs, 1H), 8.69 (s, 1H), 8.53 (d, J=4.0 Hz, 1H), 7.74 (d, J=7.8 Hz, 1H), 7.55 (s, 1H), 6.84 (t, J=5.7 Hz, 1H), 4.66 (d, J=5.6 Hz, 2H), 4.46-4.33 (m, 1H), 1.84 (p, J=12.6 Hz, 7H), 1.37 (ddd, J=61.4, 19.9, 11.1 Hz, 3H).

Example 74

Synthesis of Compound WYQ-60

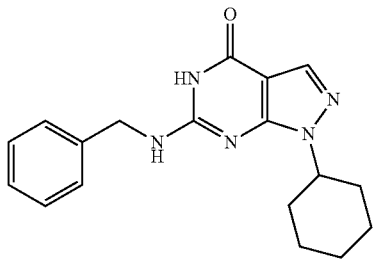
WYQ-60

The synthesis method was the same as that for the method for the synthesis of compound WYQ-49 in Example 63. Compound M-6 (76 mg, 0.3 mmol), benzylamine (64 mg, 0.6 mmol), and isopropanol (5 ml) were reacted. The reaction product was separated and purified, and finally white solids (69 mg, 71%) were obtained.

MS (ESI$^-$): m/z: 322 ([M–H]$^-$); $^1$H NMR (400 MHz, CDCl$_3$) δ 10.97 (brs, 1H), 7.45-7.30 (m, 6H), 6.95 (brs, 1H), 4.68 (d, J=4.6 Hz, 2H), 4.53-4.40 (m, 1H), 2.01-1.72 (m, 7H), 1.52-1.31 (m, 3H).

Example 75

Synthesis of Compound WYQ-61

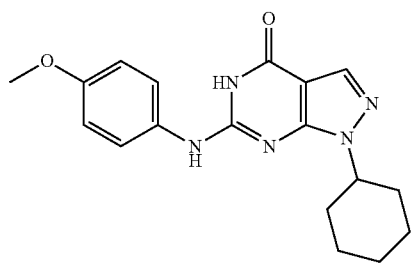
WYQ-61

The synthesis method was the same as that for the method for the synthesis of compound WYQ-49 in Example 63. Compound M-6 (76 mg, 0.3 mmol), 4-methoxybenzenamine (111 mg, 0.9 mmol), and isopropanol (3 ml) were reacted. The reaction product was separated and purified, and finally white solids (76 mg, 74%) were obtained.

MS (ESI$^-$): m/z: 338 ([M–H]$^-$); $^1$H NMR (400 MHz, CDCl$_3$) δ 10.52 (brs, 1H), 8.67 (s, 1H), 7.86 (s, 1H), 7.60-7.52 (m, 2H), 6.94 (d, J=9.0 Hz, 2H), 4.51-4.39 (m, 1H), 3.84 (s, 3H), 2.01-1.72 (m, 7H), 1.48-1.27 (m, 3H).

Example 76

Synthesis of Compound WYQ-62

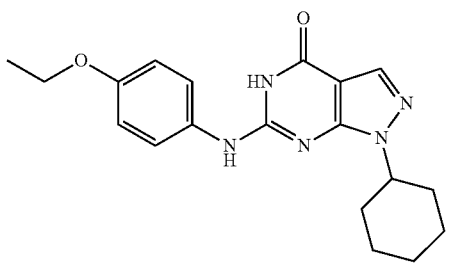
WYQ-62

The synthesis method was the same as that for the method for the synthesis of compound WYQ-49 in Example 63. Compound M-6 (76 mg, 0.3 mmol), 4-ethoxybenzenamine (123 mg, 0.9 mmol), and isopropanol (2 ml) were reacted. The reaction product was separated and purified, and finally white solids (74 mg, 70%) were obtained.

MS (ESI$^-$): m/z: 352 ([M–H]$^-$); $^1$H NMR (400 MHz, CDCl$_3$) δ 10.56 (brs, 1H), 8.75 (brs, 1H), 7.84 (s, 1H), 7.55 (d, J=9.0 Hz, 2H), 6.91 (d, J=9.0 Hz, 2H), 4.49-4.37 (m, 1H), 4.05 (q, J=7.0 Hz, 2H), 2.01-1.72 (m, 7H), 1.45 (d, J=7.0 Hz, 3H), 1.47-1.25 (m, 3H).

Example 77

Synthesis of Compound WYQ-63

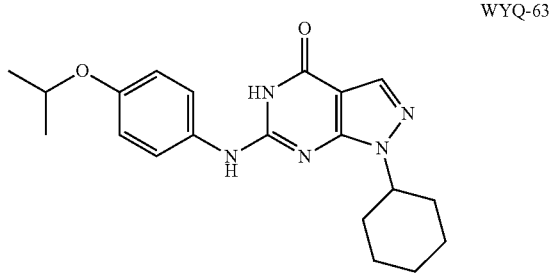 [SMILES: CC(C)Oc1ccc(Nc2nc3c(cnn3C3CCCCC3)c(=O)[nH]2)cc1]
WYQ-63

The synthesis method was the same as that for the method for the synthesis of compound WYQ-49 in Example 63. Compound M-6 (76 mg, 0.3 mmol), 4-isopropoxybenzenamine (136 mg, 0.9 mmol), and isopropanol (5 ml) were reacted. The reaction product was separated and purified, and finally white solids (84 mg, 76%) were obtained.

MS (ESI$^-$): m/z: 366 ([M–H]$^-$); $^1$H NMR (400 MHz, CDCl$_3$) δ 10.47 (brs, 1H), 8.62 (brs, 1H), 7.87 (s, 1H), 7.54 (d, J=9.0 Hz, 2H), 6.93 (d, J=9.0 Hz, 2H), 4.54 (dt, J=12.1, 6.1 Hz, 1H), 4.50-4.40 (m, 1H), 2.02-1.73 (m, 17H), 1.36 (d, J=6.1 Hz, 6H), 1.47-1.26 (m, 3H).

Example 78

Synthesis of Compound WYQ-64

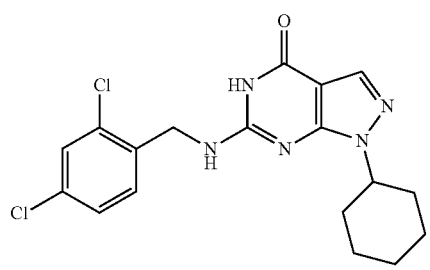
WYQ-64

The synthesis method was the same as that for the method for the synthesis of compound WYQ-49 in Example 63. Compound M-6 (76 mg, 0.3 mmol), 2,4-dichlorobenzylamine (106 mg, 0.6 mmol), and isopropanol (4 ml) were reacted. The reaction product was separated and purified, and finally white solids (90 mg, 77%) were obtained.

MS (ESI⁻): m/z: 390 ([M–H]⁻); ¹H NMR (400 MHz, DMSO) δ 10.59 (brs, 1H), 7.71 (s, 1H), 7.59 (d, J=2.1 Hz, 1H), 7.47 (d, J=8.3 Hz, 1H), 7.37 (dd, J=8.3, 2.1 Hz, 1H), 7.12 (t, J=5.7 Hz, 1H), 4.56 (d, J=5.8 Hz, 2H), 4.32-4.20 (m, 1H), 1.80-1.62 (m, 7H), 1.35 (dd, J=9.2, 3.3 Hz, 2H), 1.16 (d, J=13.8 Hz, 1H).

Example 79

Synthesis of Compound WYQ-65

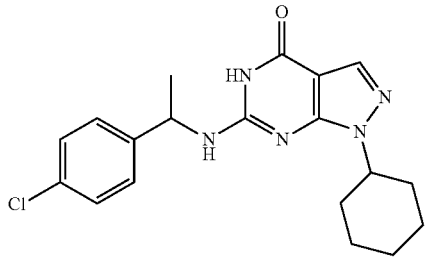

WYQ-65

The synthesis method was the same as that for the method for the synthesis of compound WYQ-49 in Example 63. Compound M-6 (76 mg, 0.3 mmol), 1-(4-chlorphenyl)ethylamine (93 mg, 0.6 mmol), and isopropanol (3 ml) were reacted. The reaction product was separated and purified, and finally white solids (63 mg, 57%) were obtained.

MS (ESI⁻): m/z: 370 ([M–H]⁻); ¹H NMR (400 MHz, CDCl₃) δ 10.76 (brs, 1H), 7.67 (s, 1H), 7.36-7.32 (m, 2H), 7.30-7.26 (m, 2H), 6.98 (d, J=6.6 Hz, 1H), 5.12 (p, J=6.8 Hz, 1H), 4.30 (tt, J=9.5, 4.6 Hz, 1H), 1.93-1.76 (m, 7H), 1.61 (d, J=7.0 Hz, 3H), 1.44-1.27 (m, 3H).

Example 80

Synthesis of Compound WYQ-66

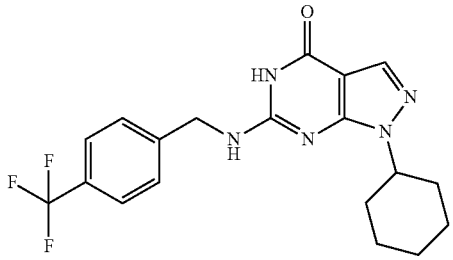

WYQ-66

The synthesis method was the same as that for the method for the synthesis of compound WYQ-49 in Example 63. Compound M-6 (76 mg, 0.3 mmol), 4-trifluoromethylbenzylamine (105 mg, 0.6 mmol), and isopropanol (1 ml) were reacted. The reaction product was separated and purified, and finally white solids (40 mg, 34%) were obtained.

MS (ESI⁻): m/z: 390 ([M–H]⁻); ¹H NMR (400 MHz, DMSO) δ 10.68 (brs, 1H), 7.70 (s, 1H), 7.68 (d, J=8.1 Hz, 2H), 7.58 (d, J=8.1 Hz, 2H), 7.13 (t, J=5.7 Hz, 1H), 4.59 (d, J=5.7 Hz, 2H), 4.28-4.15 (m, 1H), 1.81-1.61 (m, 7H), 1.35-1.12 (m, 3H).

Example 81

Synthesis of Compound WYQ-67

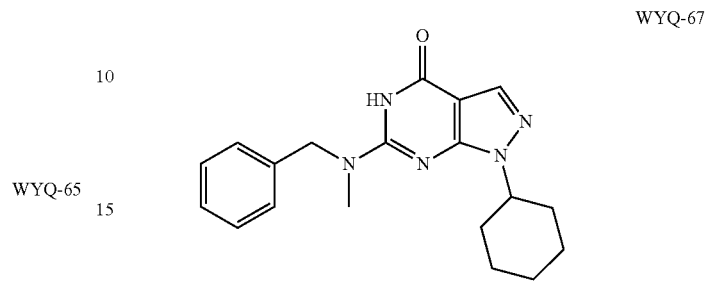

WYQ-67

The synthesis method was the same as that for the method for the synthesis of compound WYQ-49 in Example 63. Compound M-6 (76 mg, 0.3 mmol), N-methylbenzylamine (73 mg, 0.6 mmol), and isopropanol (2 ml) were reacted. The reaction product was separated and purified, and finally white solids (62 mg, 61%) were obtained.

MS (ESI⁻): m/z: 336 ([M–H]⁻); ¹H NMR (400 MHz, CDCl₃) δ 10.29 (brs, 1H), 7.80 (s, 1H), 7.36-7.27 (m, 5H), 4.86 (s, 2H), 4.43 (dt, J=15.6, 8.7 Hz, 1H), 3.20 (s, 3H), 1.99-1.68 (m, 7H), 1.46-1.26 (m, 3H).

Example 82

Synthesis of Compound WYQ-68

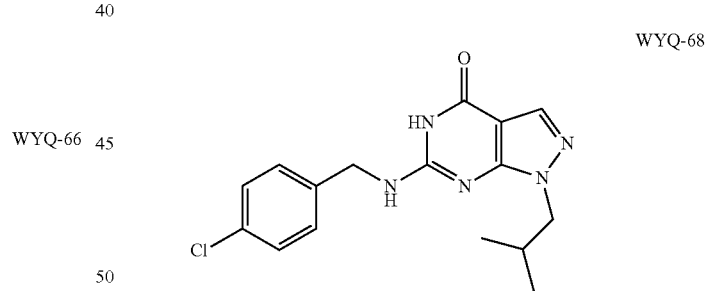

WYQ-68

Compound M-8 (68 mg, 0.3 mmol) obtained in Example 8, 4-chlorobenzylamine (85 mg, 0.6 mmol), triethylamine (40 mg, 0.4 mmol), and isopropanol (4 ml) were added into a reaction tube, and were reacted at 100° C. for 1 hour after the tube was sealed. After the reaction, the solvent was removed by rotatary evaporation. The reaction product was separated and purified via column chromatography (CH₂Cl₂:MeOH=20:1), and finally, white solids were obtained (66 mg, 66%).

MS (ESI⁻): m/z: 330 ([M–H]⁻); ¹H NMR (400 MHz, DMSO) δ 10.59 (brs, 1H), 7.74 (s, 1H), 7.41-7.33 (m, 4H), 7.03 (t, J=5.7 Hz, 1H), 4.49 (d, J=5.9 Hz, 2H), 3.85 (d, J=7.1 Hz, 2H), 2.07 (dp, J=13.6, 6.8 Hz, 1H), 0.76 (d, J=6.7 Hz, 6H).

Example 83

Synthesis of Compound WYQ-69

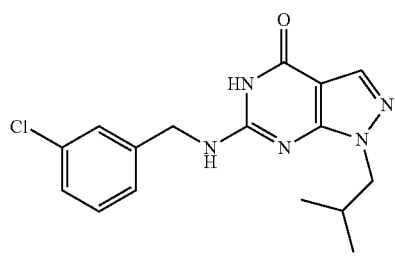

WYQ-69

The synthesis method was the same as that for the method for the synthesis of compound WYQ-68 in Example 82. Compound M-8 (68 mg, 0.3 mmol), 3-chlorobenzylamine (85 mg, 0.6 mmol), and isopropanol (2 ml) were reacted. The reaction product was separated and purified, and finally white solids (70 mg, 70%) were obtained.

MS (ESI$^-$): m/z: 330 ([M−H]$^-$); $^1$H NMR (400 MHz, DMSO) δ 10.62 (brs, 1H), 7.74 (s, 1H), 7.46-7.41 (m, 1H), 7.35-7.27 (m, 3H), 7.07 (t, J=5.8 Hz, 1H), 4.49 (d, J=5.9 Hz, 2H), 3.86 (d, J=7.2 Hz, 2H), 2.09 (dp, J=13.7, 6.8 Hz, 1H), 0.76 (d, J=6.7 Hz, 6H).

Example 84

Synthesis of Compound WYQ-70

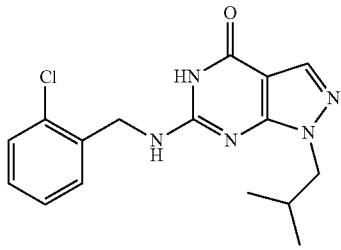

WYQ-70

The synthesis method was the same as that for the method for the synthesis of compound WYQ-68 in Example 82. Compound M-8 (68 mg, 0.3 mmol), 2-chlorobenzylamine (85 mg, 0.6 mmol), and isopropanol (2 ml) were reacted. The reaction product was separated and purified, and finally white solids (64 mg, 64%) were obtained.

MS (ESI$^-$): m/z: 330 ([M−H]$^-$); $^1$H NMR (400 MHz, DMSO) δ 10.53 (brs, 1H), 7.74 (s, 1H), 7.45 (ddd, J=7.2, 4.1, 2.7 Hz, 2H), 7.32-7.25 (m, 2H), 7.08 (t, J=5.8 Hz, 1H), 4.59 (d, J=5.9 Hz, 2H), 3.86 (d, J=7.1 Hz, 2H), 2.06 (dp, J=13.7, 6.8 Hz, 1H), 0.74 (d, J=6.7 Hz, 6H).

Example 85

Synthesis of Compound WYQ-71

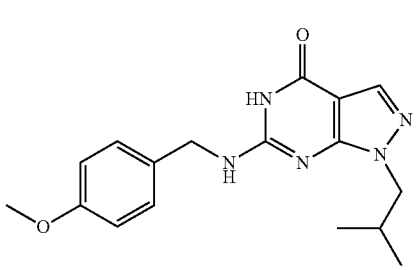

WYQ-71

The synthesis method was the same as that for the method for the synthesis of compound WYQ-68 in Example 82. Compound M-8 (68 mg, 0.3 mmol), 4-methoxybenzylamine (83 mg, 0.6 mmol), and isopropanol (5 ml) were reacted. The reaction product was separated and purified, and finally white solids (74 mg, 75%) were obtained.

MS (ESI$^-$): m/z: 326 ([M−H]$^-$); $^1$H NMR (400 MHz, CDCl$_3$) δ 10.89 (brs, 1H), 7.37 (s, 1H), 7.34-7.29 (m, 2H), 6.91-6.85 (m, 2H), 6.79 (brs, 1H), 4.57 (d, J=5.1 Hz, 2H), 4.00 (d, J=7.2 Hz, 2H), 3.80 (s, 3H), 2.28 (dp, J=13.7, 6.8 Hz, 1H), 0.91 (d, J=6.7 Hz, 6H).

Example 86

Synthesis of Compound WYQ-72

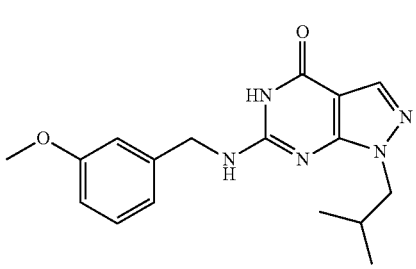

WYQ-72

The synthesis method was the same as that for the method for the synthesis of compound WYQ-68 in Example 82. Compound M-8 (68 mg, 0.3 mmol), 3-methoxybenzylamine (83 mg, 0.6 mmol), and isopropanol (4 ml) were reacted. The reaction product was separated and purified, and finally white solids (66 mg, 67%) were obtained.

MS (ESI$^-$): m/z: 326 ([M−H]$^-$); $^1$H NMR (400 MHz, CDCl$_3$) δ 10.91 (brs, 1H), 7.34 (s, 1H), 7.30-7.25 (m, 1H), 7.00-6.92 (m, 2H), 6.85 (dd, J=8.2, 2.0 Hz, 1H), 4.62 (d, J=4.9 Hz, 2H), 3.99 (d, J=7.3 Hz, 2H), 3.77 (s, 3H), 2.27 (dp, J=13.7, 6.8 Hz, 1H), 0.89 (d, J=6.7 Hz, 6H).

Example 87

Synthesis of Compound WYQ-73

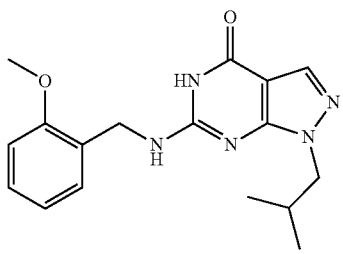

WYQ-73

The synthesis method was the same as that for the method for the synthesis of compound WYQ-68 in Example 82. Compound M-8 (68 mg, 0.3 mmol), 2-methoxybenzylamine (83 mg, 0.6 mmol), and isopropanol (3 ml) were reacted. The reaction product was separated and purified, and finally white solids (71 mg, 72%) were obtained.

MS (ESI$^-$): m/z: 326 ([M−H]$^-$); $^1$H NMR (400 MHz, CDCl$_3$) δ 10.91 (brs, 1H), 7.54 (s, 1H), 7.40 (dd, J=7.4, 1.6 Hz, 1H), 7.32-7.26 (m, 1H), 6.91 (ddd, J=8.2, 6.6, 2.9 Hz, 2H), 4.63 (d, J=5.7 Hz, 2H), 4.03 (d, J=7.3 Hz, 2H), 3.83 (s, 3H), 2.31 (dp, J=13.7, 6.9 Hz, 1H), 0.93 (d, J=6.7 Hz, 6H).

Example 88

Synthesis of Compound WYQ-74

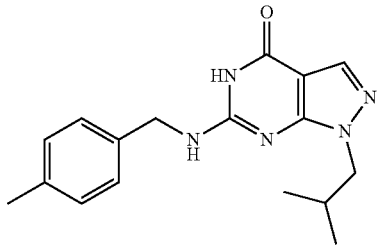

WYQ-74

The synthesis method was the same as that for the method for the synthesis of compound WYQ-68 in Example 82. Compound M-8 (68 mg, 0.3 mmol), 4-methylbenzylamine (73 mg, 0.6 mmol), and isopropanol (3 ml) were reacted. The reaction product was separated and purified, and finally white solids (70 mg, 75%) were obtained.

MS (ESI$^-$): m/z: 310 ([M−H]$^-$; $^1$H NMR (400 MHz, DMSO) δ 10.45 (brs, 1H), 7.74 (s, 1H), 7.26 (d, J=7.9 Hz, 2H), 7.12 (d, J=7.8 Hz, 2H), 6.93 (t, J=5.5 Hz, 1H), 4.45 (d, J=5.7 Hz, 2H), 3.88 (d, J=7.1 Hz, 2H), 2.26 (s, 3H), 2.12 (dp, J=13.6, 6.8 Hz, 1H), 0.80 (d, J=6.7 Hz, 6H).

Example 89

Synthesis of Compound WYQ-75

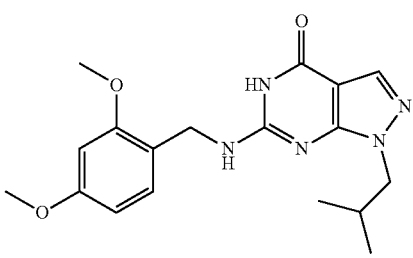

WYQ-75

The synthesis method was the same as that for the method for the synthesis of compound WYQ-68 in Example 82. Compound M-8 (68 mg, 0.3 mmol), 2,5-dimethoxybenzylamine (100 mg, 0.6 mmol), and isopropanol (2 ml) were reacted. The reaction product was separated and purified, and finally white solids (74 mg, 69%) were obtained.

MS (ESI$^-$): m/z: 356 ([M−H]$^-$); $^1$H NMR (400 MHz, CDCl$_3$) δ 10.92 (brs, 1H), 7.63 (s, 1H), 7.30 (d, J=8.2 Hz, 1H), 6.72 (brs, 1H), 6.49-6.39 (m, 2H), 4.55 (d, J=5.8 Hz, 2H), 4.03 (d, J=7.2 Hz, 2H), 3.80 (d, J=5.1 Hz, 6H), 2.31 (dp, J=13.6, 6.8 Hz, 1H), 0.94 (d, J=6.7 Hz, 6H).

Example 90

Synthesis of Compound WYQ-76

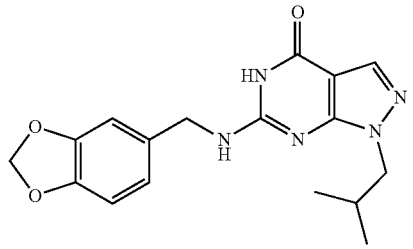

WYQ-76

The synthesis method was the same as that for the method for the synthesis of compound WYQ-68 in Example 82. Compound M-8 (68 mg, 0.3 mmol), 3,4-methylenedioxybenzylamine (68 mg, 0.45 mmol), and isopropanol (2 ml) were reacted. The reaction product was separated and purified, and finally white solids (73 mg, 72%) were obtained.

MS (ESI$^-$): m/z: 3406 ([M−H]$^-$); $^1$H NMR (400 MHz, DMSO) δ 10.45 (brs, 1H), 7.74 (s, 1H), 6.96 (s, 1H), 6.91 (t, J=5.5 Hz, 1H), 6.88-6.82 (m, 2H), 5.97 (s, 2H), 4.40 (d, J=5.8 Hz, 2H), 3.90 (d, J=7.1 Hz, 2H), 2.13 (dp, J=13.6, 6.8 Hz, 1H), 0.81 (d, J=6.7 Hz, 6H).

Example 91

Synthesis of Compound WYQ-77

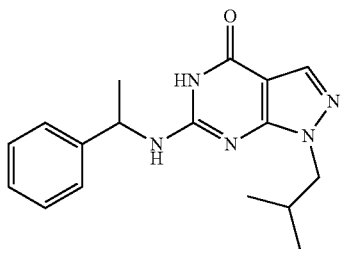

The synthesis method was the same as that for the method for the synthesis of compound WYQ-68 in Example 82. Compound M-8 (68 mg, 0.3 mmol), α-methylbenzylamine (73 mg, 0.6 mmol), and isopropanol (6 ml) were reacted. The reaction product was separated and purified, and finally white solids (52 mg, 54%) were obtained.

MS (ESI$^-$): m/z: 310 ([M−H]$^-$); $^1$H NMR (400 MHz, CDCl$_3$) δ 10.66 (brs, H), 7.48 (s, H), 7.43-7.39 (m, 2H), 7.36-7.29 (m, 2H), 7.29-7.21 (m, 1H), 7.16 (d, J=6.9 Hz, 1H), 5.20 (p, J=6.8 Hz, 1H), 4.00-3.88 (m, 2H), 2.28-2.11 (m, 1H), 1.64 (d, J=6.9 Hz, 3H), 0.85 (dd, J=28.4, 6.7 Hz, 6H).

Example 92

Synthesis of Compound WYQ-78

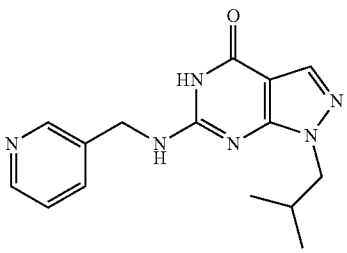

The synthesis method was the same as that for the method for the synthesis of compound WYQ-68 in Example 82. Compound M-8 (68 mg, 0.3 mmol), 3-pyridinebenzylamine (65 mg, 0.6 mmol), and isopropanol (0.6 ml) were reacted. The reaction product was separated and purified, and finally white solids (54 mg, 60%) were obtained.

MS (ESI$^-$): m/z: 297 ([M−H]$^-$); $^1$H NMR (400 MHz, DMSO) δ 10.64 (brs, 1H), 8.61 (d, J=1.5 Hz, 1H), 8.45 (dd, J=4.7, 1.3 Hz, 1H), 7.77 (m, 1H), 7.74 (s, 1H), 7.34 (dd, J=7.8, 4.8 Hz, 1H), 7.09 (t, J=5.7 Hz, 1H), 4.51 (d, J=5.8 Hz, 2H), 3.86 (d, J=7.1 Hz, 2H), 2.07 (dp, J=13.7, 6.9 Hz, 1H), 0.76 (d, J=6.7 Hz, 6H).

Example 93

Synthesis of Compound WYQ-79

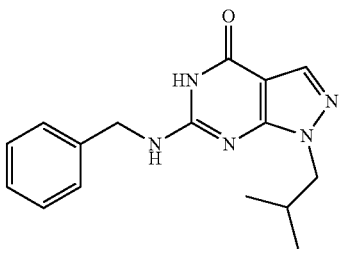

The synthesis method was the same as that for the method for the synthesis of compound WYQ-68 in Example 82. Compound M-8 (68 mg, 0.3 mmol), benzylamine (64 mg, 0.6 mmol), and isopropanol (4 ml) were reacted. The reaction product was separated and purified, and finally white solids (58 mg, 65%) were obtained.

MS (ESI$^-$): m/z: 296 ([M−H]$^-$); $^1$H NMR (400 MHz, DMSO) δ 10.50 (brs, 1H), 7.75 (s, 1H), 7.40-7.30 (m, 4H), 7.25 (ddd, J=7.1, 3.8, 1.4 Hz, 1H), 7.00 (t, J=5.6 Hz, 1H), 4.51 (d, J=5.8 Hz, 2H), 3.88 (d, J=7.1 Hz, 2H), 2.11 (dp, J=13.7, 6.8 Hz, 1H), 0.79 (d, J=6.7 Hz, 6H).

Example 94

Synthesis of Compound WYQ-80

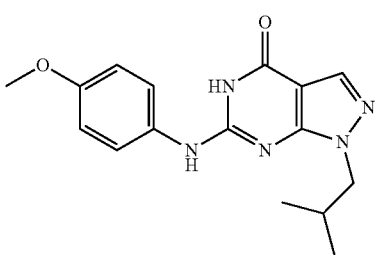

The synthesis method was the same as that for the method for the synthesis of compound WYQ-68 in Example 82. Compound M-8 (68 mg, 0.3 mmol), 4-methoxy (111 mg, 0.9 mmol), and isopropanol (1 ml) were reacted. The reaction product was separated and purified, and finally white solids (75 mg, 80%) were obtained.

MS (ESI$^-$): m/z: 312 ([M−H]$^-$); $^1$H NMR (400 MHz, CDCl$_3$) δ 8.64 (s, 1H), 7.90 (s, 1H), 7.55 (d, J=8.4 Hz, 2H), 6.94 (d, J=8.2 Hz, 2H), 4.04 (d, J=6.8 Hz, 2H), 3.84 (s, 3H), 2.36-2.28 (m, 1H), 0.96 (d, J=6.6 Hz, 6H).

Example 95

Synthesis of Compound WYQ-81

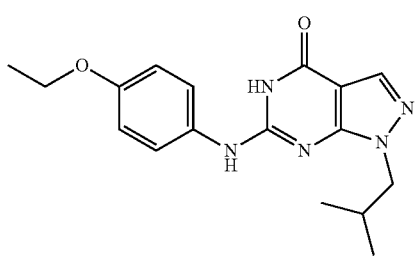

WYQ-81

The synthesis method was the same as that for the method for the synthesis of compound WYQ-68 in Example 82. Compound M-8 (68 mg, 0.3 mmol), 4-ethoxy (123 mg, 0.9 mmol), and isopropanol (2 ml) were reacted. The reaction product was separated and purified, and finally white solids (60 mg, 60%) were obtained.

MS (ESI$^-$): m/z: 326 ([M−H]$^-$); $^1$H NMR (400 MHz, CDCl$_3$) δ 10.60 (brs, 1H), 8.69 (brs, 1H), 7.86 (s, 1H), 7.55 (d, J=8.9 Hz, 2H), 6.92 (d, J=8.9 Hz, 2H), 4.09-3.97 (m, 4H), 2.31 (dp, J=13.4, 6.7 Hz, 1H), 1.44 (t, J=7.0 Hz, 3H), 0.95 (d, J=6.7 Hz, 6H).

Example 96

Synthesis of Compound WYQ-82

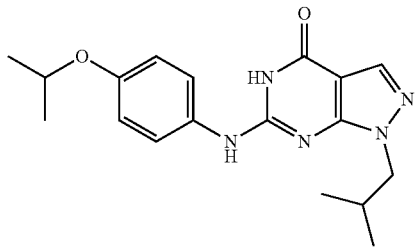

WYQ-82

The synthesis method was the same as that for the method for the synthesis of compound WYQ-68 in Example 82. Compound M-8 (68 mg, 0.3 mmol), 4-isopropoxy (136 mg, 0.9 mmol), and isopropanol (2 ml) were reacted. The reaction product was separated and purified, and finally white solids (70 mg, 68%) were obtained.

MS (ESI$^-$): m/z: 340 ([M−H]$^-$); $^1$H NMR (400 MHz, CDCl$_3$) δ 10.51 (brs, 1H), 8.69 (brs, 1H), 7.89 (s, 1H), 7.53 (d, J=8.5 Hz, 2H), 6.92 (d, J=8.4 Hz, 2H), 4.54 (dt, J=12.0, 6.0 Hz, 1H), 4.03 (d, J=7.1 Hz, 2H), 2.32 (dt, J=13.6, 6.8 Hz, 1H), 1.36 (d, J=6.0 Hz, 6H), 0.95 (d, J=6.6 Hz, 6H).

Example 97

Synthesis of Compound WYQ-83

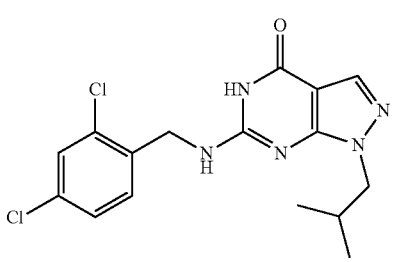

WYQ-83

The synthesis method was the same as that for the method for the synthesis of compound WYQ-68 in Example 82. Compound M-8 (68 mg, 0.3 mmol), 2,4-dichlorobenzylamine (132 mg, 0.75 mmol), and isopropanol (1 ml) were reacted. The reaction product was separated and purified, and finally white solids (74 mg, 67%) were obtained.

MS (ESI$^-$): m/z: 364 ([M−H]$^-$); $^1$H NMR (400 MHz, DMSO) δ 10.46 (brs, 1H), 7.74 (s, 1H), 7.59 (d, J=2.1 Hz, 1H), 7.46 (d, J=8.3 Hz, 1H), 7.38 (dd, J=8.3, 2.1 Hz, 1H), 7.13 (t, J=5.8 Hz, 1H), 4.56 (d, J=5.8 Hz, 2H), 3.84 (d, J=7.1 Hz, 2H), 2.03 (dp, J=13.7, 6.8 Hz, 1H), 0.73 (d, J=6.7 Hz, 6H).

Example 98

Synthesis of Compound WYQ-84

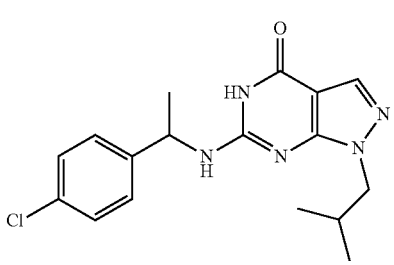

WYQ-84

The synthesis method was the same as that for the method for the synthesis of compound WYQ-68 in Example 82. Compound M-8 (68 mg, 0.3 mmol), 1-(4-chlorophenyl)ethylamine (93 mg, 0.6 mmol), and isopropanol (2 ml) were reacted. The reaction product was separated and purified, and finally white solids (61 mg, 58%) were obtained.

MS (ESI$^-$): m/z: 344 ([M−H]$^-$); $^1$H NMR (400 MHz, CDCl$_3$) δ 10.79 (brs, 1H), 7.65 (s, 1H), 7.31 (td, J=8.6, 6.5 Hz, 4H), 6.88 (d, J=6.7 Hz, 1H), 5.13 (p, J=6.8 Hz, 1H), 3.96-3.85 (m, 2H), 2.21-2.10 (m, 1H), 1.61 (d, J=7.0 Hz, 3H), 0.87 (d, J=6.7 Hz, 3H), 0.79 (d, J=6.7 Hz, 3H).

Example 99

Synthesis of Compound WYQ-85

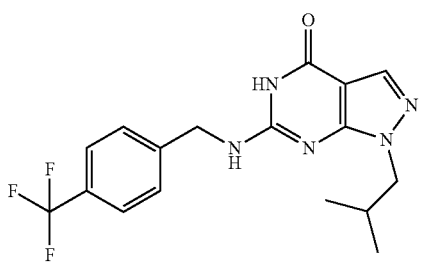

WYQ-85

The synthesis method was the same as that for the method for the synthesis of compound WYQ-68 in Example 82. Compound M-8 (68 mg, 0.3 mmol), 4-trifluoromethylbenzylamine (105 mg, 0.6 mmol), and isopropanol (5 ml) were reacted. The reaction product was separated and purified, and finally white solids (59 mg, 54%) were obtained.

MS (ESI$^-$): m/z: 364 ([M−H]$^-$); $^1$H NMR (400 MHz, DMSO) δ 10.73 (brs, 1H), 7.74 (s, 1H), 7.67 (d, J=8.2 Hz, 2H), 7.56 (d, J=8.1 Hz, 2H), 7.16 (t, J=5.6 Hz, 1H), 4.58 (d, J=5.8 Hz, 2H), 3.80 (d, J=7.2 Hz, 2H), 1.98 (dt, J=13.6, 6.8 Hz, 1H), 0.67 (d, J=6.7 Hz, 6H).

Example 100

Synthesis of Compound WYQ-86

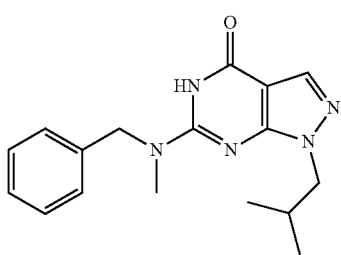

WYQ-86

The synthesis method was the same as that for the method for the synthesis of compound WYQ-68 in Example 82. Compound M-8 (68 mg, 0.3 mmol), N-methylbenzylamine (73 mg, 0.6 mmol), and isopropanol (4 ml) were reacted. The reaction product was separated and purified, and finally white solids (39 mg, 42%) were obtained.

MS (ESI$^-$): m/z: 310 ([M−H]$^-$)$^1$H NMR (400 MHz, DMSO) δ 7.78 (s, 1H), 7.37-7.22 (m, 5H), 4.80 (s, 2H), 3.88 (d, J=7.1 Hz, 2H), 3.08 (s, 3H), 2.11 (dp, J=13.6, 6.8 Hz, 1H), 0.79 (d, J=6.7 Hz, 6H).

Example 101

Synthesis of Compound WYQ-87-D

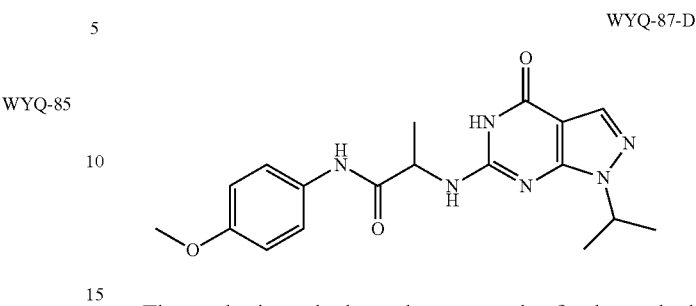

WYQ-87-D

The synthesis method was the same as that for the method for the synthesis of compound WYQ-1 in Example 1. The reaction product was separated and purified, and finally, white solids were obtained (55 mg, 50%).

MS (ESI$^-$): m/z: 369 ([M−H]$^-$); $^1$H NMR (400 MHz, CDCl$_3$) δ 7.87 (s, 1H), 7.41 (d, J=8.9 Hz, 2H), 6.83 (d, J=8.9 Hz, 2H), 4.85-4.78 (m, 2H), 4.70-4.62 (m, 1H), 3.77 (s, 3H), 1.58 (d, J=7.0 Hz, 3H), 1.45 (dd, J=14.9, 6.7 Hz, 6H).

Example 102

Synthesis of Compound WYQ-87-L

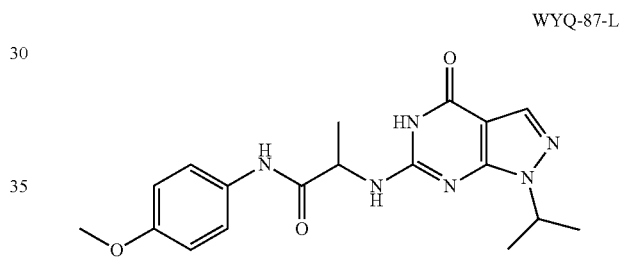

WYQ-87-L

The synthesis method was the same as that for the method for the synthesis of compound WYQ-1 in Example 1. The reaction product was separated and purified, and finally, white solids were obtained (50 mg, 45%).

MS (ESI$^-$): m/z: 369 ([M−H]$^-$); $^1$H NMR (400 MHz, DMSO) δ 10.44 (brs, 1H), 10.08 (s, 1H), 7.75 (s, 1H), 7.54-7.48 (m, 2H), 6.92 (d, J=6.9 Hz, 1H), 6.91-6.86 (m, 2H), 4.77-4.69 (m, 1H), 4.59 (p, J=6.8 Hz, 1H), 3.72 (s, 3H), 1.44 (d, J=6.9 Hz, 3H), 1.38 (d, J=6.7 Hz, 3H), 1.31 (d, J=6.7 Hz, 3H).

Example 103

Synthesis of Compound WYQ-88

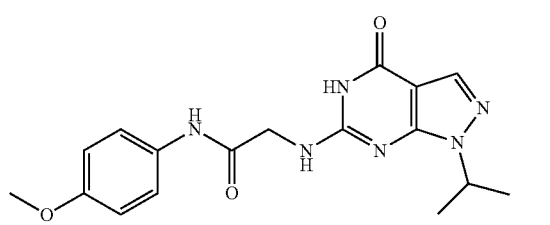

WYQ-88

The synthesis method was the same as that for the method for the synthesis of compound WYQ-1 in Example 1. The reaction product was separated and purified, and finally, white solids were obtained (39 mg, 37%)

MS (ESI⁻): m/z: 355 ([M−H]⁻); ¹H NMR (400 MHz, DMSO) δ 10.72 (s, 1H), 10.02 (s, 1H), 7.75 (s, 1H), 7.49 (d, J=9.0 Hz, 2H), 6.88 m, 3H), 4.78-4.67 (m, 1H), 4.14 (d, J=5.1 Hz, 2H), 3.72 (s, 3H), 1.36 (d, J=6.7 Hz, 6H).

Example 104

Synthesis of Compound WYQ-89

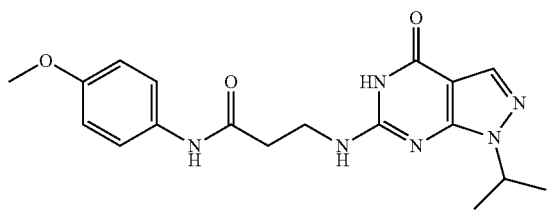

WYQ-89

The synthesis method was the same as that for the method for the synthesis of compound WYQ-1 in Example 1. The reaction product was separated and purified, and finally, white solids were obtained (50 mg, 45%).

MS (ESI⁻): m/z: 369 ([M−H]⁻); ¹H NMR (400 MHz, DMSO) δ 10.25 (s, 1H), 9.56 (s, 1H), 7.66 (s, 1H), 7.46 (d, J=8.8 Hz, 2H), 6.75 (d, J=8.7 Hz, 2H), 6.58 (s, 1H), 4.80 (dt, J=13.1, 6.6 Hz, 1H), 3.70 (d, J=1.0 Hz, 3H), 3.58 (s, 2H), 2.59 (t, J=5.3 Hz, 2H), 1.41 (dd, J=6.6, 1.1 Hz, 6H).

Example 105

Synthesis of Compound WYQ-90-D

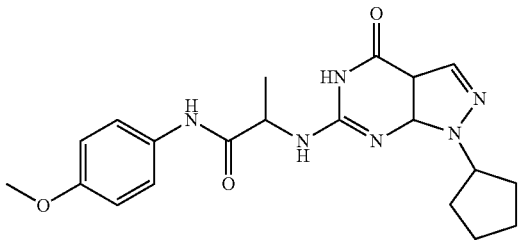

WYQ-90-D

The synthesis method was the same as that for the method for the synthesis of compound WYQ-25 in Example 39. The reaction product was separated and purified, and finally, white solids were obtained (45 mg, 38%).

MS (ESI⁻): m/z: 395 ([M−H]⁻); ¹H NMR (400 MHz, CDCl₃) δ 7.74 (s, 1H), 7.47 (d, J=9.0 Hz, 2H), 6.86 (d, J=9.1 Hz, 2H), 4.86-4.77 (m, 1H), 4.46 (q, J=6.9 Hz, 1H), 3.68 (s, 3H), 1.92 (dd, J=8.4, 5.0 Hz, 2H), 1.75 (t, J=7.2 Hz, 4H), 1.62-1.45 (m, 2H), 1.40 (d, J=7.0 Hz, 3H).

Example 106

Synthesis of Compound WYQ-90-L

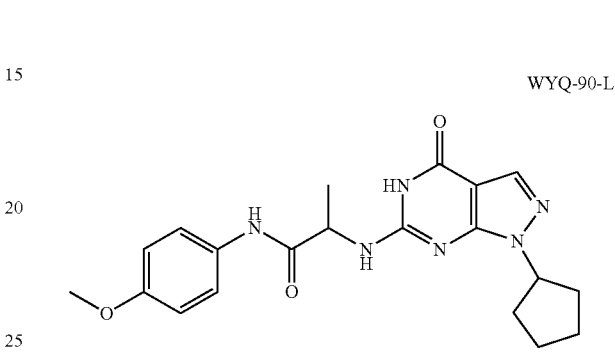

WYQ-90-L

The synthesis method was the same as that for the method for the synthesis of compound WYQ-25 in Example 39. The reaction product was separated and purified, and finally, white solids were obtained (49 mg, 42%).

MS (ESI⁻): m/z: 395 ([M−H]⁻); ¹H NMR (400 MHz, DMSO) δ 10.44 (s, 1H), 10.08 (s, 1H), 7.75 (s, 1H), 7.55-7.49 (m, 2H), 6.93-6.86 (m, 3H), 4.88 (p, J=7.3 Hz, 1H), 4.56 (p, J=6.8 Hz, 1H), 3.72 (s, 3H), 2.02-1.92 (m, 2H), 1.88-1.77 (m, 4H), 1.63-1.51 (m, 2H), 1.44 (d, J=6.9 Hz, 3H).

Example 107

Synthesis of Compound WYQ-91

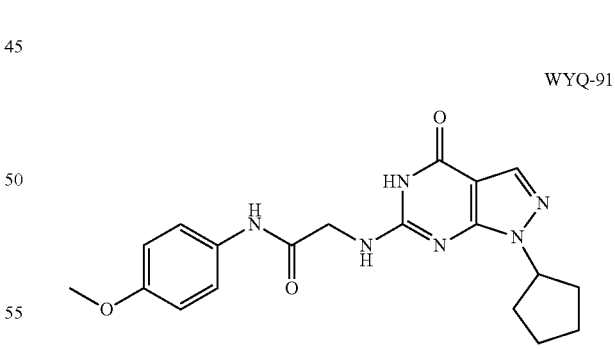

WYQ-91

The synthesis method was the same as that for the method for the synthesis of compound WYQ-25 in Example 39. The reaction product was separated and purified, and finally, white solids were obtained (39 mg, 34%).

MS (ESI⁻): m/z: 381 ([M−H]⁻); ¹H NMR (400 MHz, DMSO) δ 10.02 (s, 1H), 7.76 (s, 1H), 7.50 (d, J=9.0 Hz, 2H), 6.92-6.84 (m, 3H), 4.89 (p, J=7.4 Hz, 1H), 4.13 (d, J=5.1 Hz, 2H), 3.72 (s, 3H), 1.99-1.87 (m, 4H), 1.87-1.75 (m, 2H), 1.65-1.52 (m, 2H).

Example 108

Synthesis of Compound WYQ-92

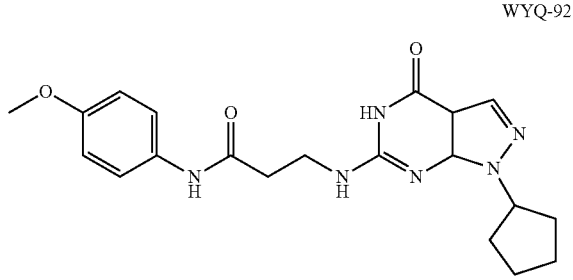 [SMILES: COc1ccc(NC(=O)CCNC2=NC3C(C=NN3C3CCCC3)C(=O)N2)cc1]

WYQ-92

The synthesis method was the same as that for the method for the synthesis of compound WYQ-25 in Example 39. The reaction product was separated and purified, and finally, white solids were obtained (43 mg, 37%).

MS (ESI⁻): m/z: 395 ([M–H]⁻); ¹H NMR (400 MHz, CDCl₃) δ 10.16 (s, 1H), 8.98 (s, 1H), 7.67 (s, 1H), 7.32 (d, J=8.8 Hz, 2H), 6.65 (d, J=8.8 Hz, 2H), 6.49 (s, 1H), 4.86 (p, J=7.5 Hz, 1H), 3.67-3.61 (m, 2H), 3.61 (s, 3H), 2.54 (t, J=5.8 Hz, 2H), 1.97-1.84 (m, 4H), 1.83-1.73 (m, 2H), 1.58-1.47 (m, 2H).

Example 109

Synthesis of Compound WYQ-93-D

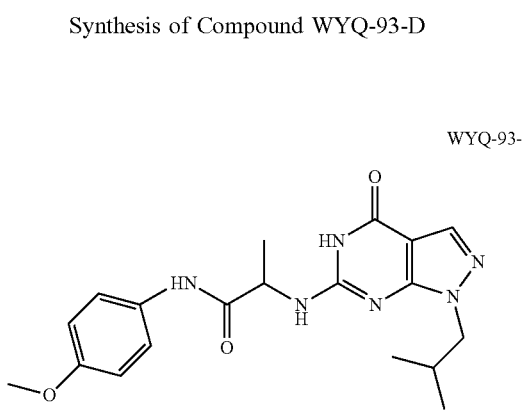

WYQ-93-D

The synthesis method was the same as that for the method for the synthesis of compound WYQ-68 in Example 82. The reaction product was separated and purified, and finally, white solids were obtained (43 mg, 37%).

MS (ESI⁻): m/z: 383 ([M–H]⁻); ¹H NMR (400 MHz, CDCl₃) δ 7.75 (s, 1H), 7.51-7.44 (m, 2H), 6.88-6.82 (m, 2H), 4.47 (q, J=6.9 Hz, 1H), 3.92-3.74 (m, 2H), 3.68 (s, 3H), 2.05 (dp, J=13.6, 6.8 Hz, 1H), 1.40 (d, J=7.0 Hz, 3H), 0.69 (d, J=6.7 Hz, 3H), 0.63 (d, J=6.7 Hz, 3H).

Example 110

Synthesis of Compound WYQ-94-D

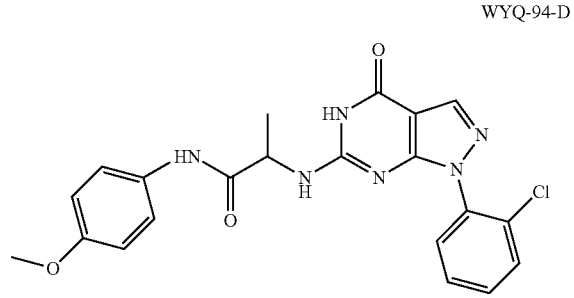 [SMILES: COc1ccc(NC(=O)C(C)Nc2nc3c(cnn3-c3ccccc3Cl)c(=O)[nH]2)cc1]

WYQ-94-D

The synthesis method was the same as that for the method for the synthesis of compound WYQ-68 in Example 82. The reaction product was separated and purified, and finally, white solids were obtained (50 mg, 38%).

MS (ESI⁻): m/z: 437 ([M–H]⁻); ¹H NMR (300 MHz, CDCl₃) δ 10.59 (brs, 1H), 8.17 (brs, 1H), 8.12 (s, 1H), 7.53-7.45 (m, 2H), 7.41-7.29 (m, 2H), 7.09 (d, J=8.9 Hz, 2H), 7.00 (d, J=5.0 Hz, 1H), 6.77 (d, J=8.9 Hz, 2H), 4.50 (p, J=6.8 Hz, 1H), 3.76 (s, 3H), 1.49 (d, J=6.9 Hz, 3H).

Example 111

Synthesis of Compound WYQ-95

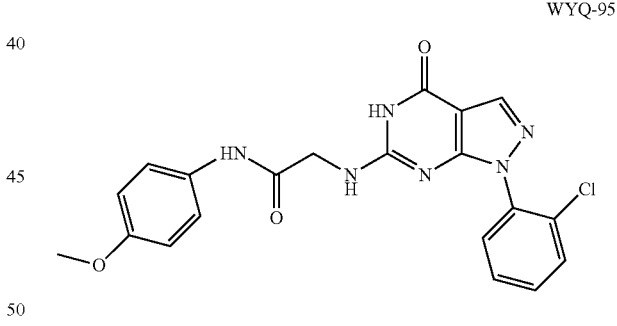

WYQ-95

The synthesis method was the same as that for the method for the synthesis of compound WYQ-68 in Example 82. The reaction product was separated and purified, and finally, white solids were obtained (43 mg, 34%).

MS (ESI⁻): m/z: 423 ([M–H]⁻); ¹H NMR (400 MHz, DMSO) δ 10.87 (brs, 1H), 9.93 (s, 1H), 8.05 (s, 1H), 7.66-7.62 (m, 1H), 7.55-7.49 (m, 2H), 7.47-7.38 (m, 3H), 7.01 (brs, 1H), 6.92-6.85 (m, 2H), 3.98 (d, J=4.7 Hz, 2H), 3.72 (s, 3H).

Inhibition activities of all the N-substituted pyrazolo [3,4-d] pyrimidine ketone compounds according to the present invention to the phosphodiesterase IX are tested. The $IC_{50}$ value is the concentration of the inhibitor when the inhibition rate reaches 50%. The test results are listed in the following table.

| Compound | IC$_{50}$ (nM) |
|---|---|
| WYQ-1 | 19 |
| WYQ-2 | 47 |
| WYQ-3 | 50 |
| WYQ-4 | 121 |
| WYQ-5 | 140 |
| WYQ-6 | 83 |
| WYQ-7 | 42 |
| WYQ-8 | 70 |
| WYQ-9 | 40 |
| WYQ-10 | 111 |
| WYQ-11 | 114 |
| WYQ-12 | 78 |
| WYQ-13 | 690 |
| WYQ-14 | 162 |
| WYQ-15 | 400 |
| WYQ-16 | 607 |
| WYQ-17 | 584 |
| WYQ-18 | 319 |
| WYQ-19 | 695 |
| WYQ-20 | 235 |
| WYQ-21 | 25 |
| WYQ-22 | 23 |
| WYQ-23 | 120 |
| WYQ-24 | 105 |
| WYQ-25 | 4 |
| WYQ-26 | 20 |
| WYQ-27 | 14 |
| WYQ-28 | 20 |
| WYQ-29 | 52 |
| WYQ-30 | 25 |
| WYQ-31 | 14 |
| WYQ-32 | 15 |
| WYQ-33 | 29 |
| WYQ-34 | 39 |
| WYQ-35 | 33 |
| WYQ-36 | 17 |
| WYQ-37 | 84 |
| WYQ-38 | 98 |
| WYQ-39 | 148 |
| WYQ-40 | 380 |
| WYQ-41 | 292 |
| WYQ-42 | 179 |
| WYQ-43 | 253 |
| WYQ-44 | 125 |
| WYQ-45 | 8 |
| WYQ-46 | 6 |
| WYQ-47 | 40 |
| WYQ-48 | 20 |
| WYQ-49 | 23 |
| WYQ-50 | 18 |
| WYQ-51 | 28 |
| WYQ-52 | 39 |
| WYQ-53 | 28 |
| WYQ-54 | 39 |
| WYQ-55 | 43 |
| WYQ-56 | 36 |
| WYQ-57 | 29 |
| WYQ-58 | 54 |
| WYQ-59 | 26 |
| WYQ-60 | 19 |
| WYQ-61 | 193 |
| WYQ-62 | 908 |
| WYQ-63 | 303 |
| WYQ-64 | 76 |
| WYQ-65 | 79 |
| WYQ-66 | 163 |
| WYQ-67 | 58 |
| WYQ-68 | 15 |
| WYQ-69 | 17 |
| WYQ-70 | 19 |
| WYQ-71 | 46 |
| WYQ-72 | 25 |
| WYQ-73 | 44 |
| WYQ-74 | 53 |
| WYQ-75 | 43 |
| WYQ-76 | 32 |
| WYQ-77 | 80 |
| WYQ-78 | 45 |
| WYQ-79 | 12 |
| WYQ-80 | 1055 |
| WYQ-81 | 743 |
| WYQ-82 | 560 |
| WYQ-83 | 21 |
| WYQ-84 | 47 |
| WYQ-85 | 121 |
| WYQ-86 | 37 |
| WYQ-87-D | 1 |
| WYQ-87-L | 303 |
| WYQ-88 | 26 |
| WYQ-89 | 26 |
| WYQ-90-D | 0.6 |
| WYQ-90-L | 3 |
| WYQ-91 | 6 |
| WYQ-92 | 6 |
| WYQ-93-D | 18 |
| WYQ-94-D | 6 |
| WYQ-95 | 52 |

As seen from the above test results, the N-substituted pyrazolo [3,4-d] pyrimidine ketone compound according to the present invention achieves an inhibition effect on the phosphodiesterase IX, and may be used as an inhibitor of the phosphodiesterase IX and have a wide application prospect.

What is claimed is:

1. A compound of formula (I):

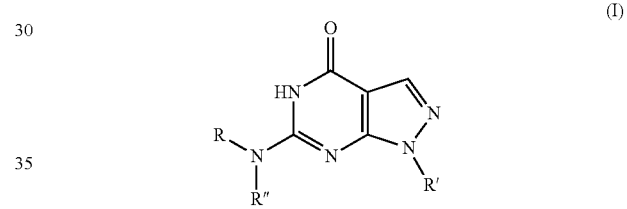

(I)

wherein

R' is selected from the group consisting of isopropyl, cyclopentyl, cyclohexyl, and isobutyl; and when R"=CH$_3$, R represents benzyl; and when R"=H, R is selected from the group consisting of L-configured CHCH$_3$CONHR''', D-configured CHCH$_3$CONHR''', L-configured CH$_2$CONHR''', D-configured CH$_2$CONHR''', L-configured CH$_2$CH$_2$CONHR''', D-configured CH$_2$CH$_2$CONHR''', 3-methylpyridine, 1-phenylethyl, 1-(4-chlorophenyl)ethyl,

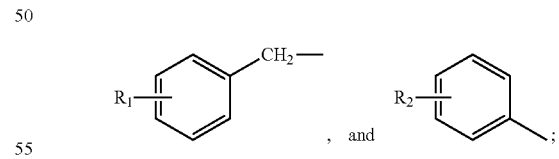

, and ;

wherein R''' is p-methoxyphenyl,

R$_1$ is selected from the group consisting of hydrogen, chlorine, methoxy, methyl, trifluoromethyl, dimethoxy, methylenedioxy, and dichlorine, and R$_2$ is selected from the group consisting of hydrogen, methoxy, ethoxy, isopropoxy, methyl, dimethoxy, and 2-methyl-4-methoxy.

2. The compound according to claim 1, wherein the compound is selected from the group consisting of compounds of formulas (II), (III), (IV), (V), (VII), (VIII), (IX), and (X):

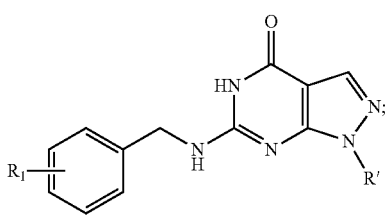

(II)

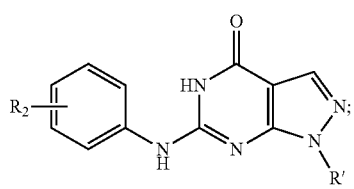

(III)

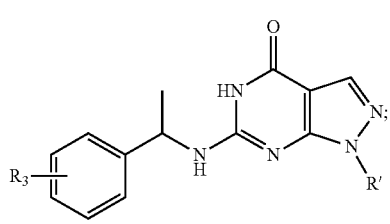

(IV)

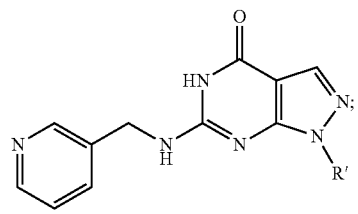

(V)

wherein
R' is selected from the group consisting of isopropyl, cyclopentyl, cyclohexyl, and isobutyl;
R₁ in formula (II) is selected from the group consisting of hydrogen, methyl, methoxy, 2,4-dimethoxy, 3,4-methylenedioxy, chlorine, 2,4-dichlorine, and trifluoromethyl;
R₂ in formula (III) is selected from the group consisting of hydrogen, methyl, methoxy, ethoxy, isopropoxy, 2-methyl-4-methoxy, and 2,5-dimethoxy; and
R₃ in formula (IV) is selected from the group consisting of hydrogen and chlorine.

3. A process for the preparation of an N-substituted pyrazolo [3,4-d] pyrimidine ketone compound as defined in claim 1, comprising the following steps:
(1) reacting using 2,4,6-trichloro-5-pyrimidinecarbaldehyde and hydrazine as starting materials, triethylamine as a base, and ethanol as a solvent at temperature −78° C. to obtain a compound A, wherein a molar ratio of 2,4,6-trichloro-5-pyrimidinecarbaldehyde to hydrazine to triethylamine is 1:1-1.1:2-3, and 2,4,6-trichloro-5-pyrimidinecarbaldehyde has a concentration of 0.05 to 1.0 mol/L,

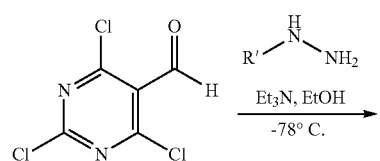

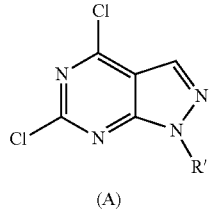

(A)

(2) hydrolyzing the compound A under a basic condition to obtain a compound B, wherein a molar ratio of the compound A to a base is 1:10-40, and the compound A has a concentration of 0.05 to 0.5 mol/L,

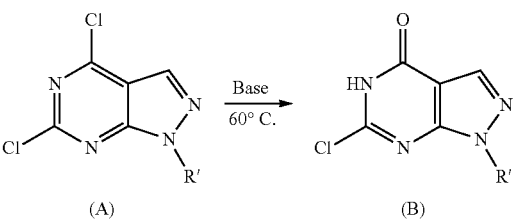

and
(3) reacting the compound B with an amine compound in the presence of triethylamine as a base to obtain a target compound I, wherein a molar ratio of the compound B to triethylamine to the amine compound is 1:1.3:1.2-3, and the compound B has a concentration of 0.05 to 0.5 mol/L,

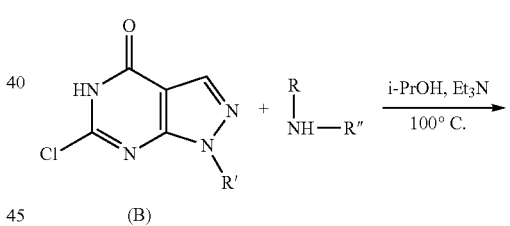

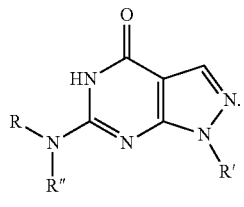

(I)

4. The process for the preparation of an N-substituted pyrazolo [3,4-d] pyrimidine ketone compound according to claim 3, wherein the base in step (2) is selected from sodium hydroxide and potassium hydroxide.

5. The process for the preparation of an N-substituted pyrazolo [3,4-d] pyrimidine ketone compound according to claim 3, wherein step (3) is performed based on heating-based tube sealing.

* * * * *